United States Patent
Makmel

(10) Patent No.: US 10,111,581 B2
(45) Date of Patent: Oct. 30, 2018

(54) THERMAL DEFOGGING SYSTEM AND METHOD

(71) Applicant: Align Technology, Inc., San Jose, CA (US)

(72) Inventor: Nir Makmel, Tel Aviv (IL)

(73) Assignee: Align Technology, Inc., San Jose, CA (US)

( * ) Notice: Subject to any disclaimer, the term of this patent is extended or adjusted under 35 U.S.C. 154(b) by 608 days.

(21) Appl. No.: 14/192,137

(22) Filed: Feb. 27, 2014

(65) Prior Publication Data

US 2015/0238072 A1 Aug. 27, 2015

(51) Int. Cl.
*A61B 1/12* (2006.01)
*A61B 1/00* (2006.01)
*H05B 3/84* (2006.01)

(52) U.S. Cl.
CPC .......... *A61B 1/127* (2013.01); *A61B 1/00163* (2013.01); *H05B 3/84* (2013.01); *H05B 2203/011* (2013.01); *H05B 2203/013* (2013.01)

(58) Field of Classification Search
CPC .... H05B 1/0227; H05B 3/0004; A61B 1/127; A61B 1/05
USPC .................. 219/549, 219, 543, 512; 356/603
See application file for complete search history.

(56) References Cited

U.S. PATENT DOCUMENTS

| | | | | | |
|---|---|---|---|---|---|
| 2,442,913 | A | * | 6/1948 | Abrams | G03B 17/55 219/203 |
| 2,564,836 | A | * | 8/1951 | Elsenheimer | A47G 1/02 219/219 |
| 3,597,586 | A | * | 8/1971 | Rebovich | H05B 3/845 219/201 |
| 3,981,021 | A | * | 9/1976 | Beecher | G03B 17/48 396/432 |

(Continued)

FOREIGN PATENT DOCUMENTS

EP 1955642 A1 8/2008
FR 2917939 A1 12/2008

(Continued)

OTHER PUBLICATIONS

International Search Report and Written Opinion for PCT/IB2015/000213 dated Jul. 28, 2015.

(Continued)

*Primary Examiner* — Jimmy Chou
(74) *Attorney, Agent, or Firm* — Lowenstein Sandler LLP

(57) ABSTRACT

A thermal defogging system and method for an optical instrument is described. In one embodiment, the thermal defogging system for an optical instrument is comprised of: at least a primary housing, the primary housing defining an aperture for transmission of optical signals, a transparent element adapted to be aligned with the aperture for transmission of optical signals, at least one side of the transparent element facing the external environment; and a transparent conductive layer covering an area at least as large as the optical footprint of the transmitted optical signal through the (Continued)

transparent element, wherein responsive to the application of electrical power to the transparent conductive layer, the transparent conductive layer generates heat that is thermally communicated to the least one side of the transparent element facing the external environment.

13 Claims, 11 Drawing Sheets

(56) References Cited

U.S. PATENT DOCUMENTS

| | | | | |
|---|---|---|---|---|
| 4,023,029 A * | 5/1977 | Fischer | ............... | G01C 3/22 359/838 |
| 4,726,656 A * | 2/1988 | Schofield | ............... | B60R 1/089 359/603 |
| 4,906,085 A * | 3/1990 | Sugihara | ............... | B60R 1/08 359/839 |
| 5,251,025 A | 10/1993 | Cooper et al. | | |
| 5,466,911 A * | 11/1995 | Spagnoli | ............... | H05B 3/84 219/203 |
| 5,482,047 A | 1/1996 | Nordgren et al. | | |
| 5,729,003 A * | 3/1998 | Briggs, III | ............... | G06K 7/10881 219/201 |
| D414,867 S | 10/1999 | Moriwaki et al. | | |
| 6,019,721 A | 2/2000 | Holmes et al. | | |
| 6,257,746 B1 * | 7/2001 | Todd | ............... | F21S 48/215 362/140 |
| 6,263,234 B1 * | 7/2001 | Engelhardt | ............... | A61B 5/0088 250/559.22 |
| 6,563,086 B1 * | 5/2003 | Meirndorf | ............... | F21S 48/1233 219/202 |
| 6,650,457 B2 * | 11/2003 | Busscher | ............... | B60Q 1/2665 359/265 |
| 6,717,109 B1 * | 4/2004 | Macher | ............... | B60R 1/0602 219/219 |
| 6,977,732 B2 * | 12/2005 | Chen | ............... | G01B 11/25 356/603 |
| D532,906 S | 11/2006 | Kim et al. | | |
| 7,244,912 B1 * | 7/2007 | Rawlings | ............... | B60R 1/0602 219/219 |
| D558,345 S | 12/2007 | Witt | | |
| 7,680,373 B2 | 3/2010 | Melville et al. | | |
| 7,858,905 B2 * | 12/2010 | Rawlings | ............... | B60R 1/0602 219/202 |
| D630,747 S | 1/2011 | Shinohara et al. | | |
| 7,914,162 B1 * | 3/2011 | Huang | ............... | B60L 1/14 219/220 |
| 8,258,433 B2 * | 9/2012 | Byers | ............... | B60R 1/088 219/219 |
| 8,459,848 B2 * | 6/2013 | Marley | ............... | G02B 27/0006 362/457 |
| D722,164 S | 2/2015 | Graham et al. | | |
| D742,518 S | 11/2015 | Barak et al. | | |
| D742,531 S | 11/2015 | Pippel et al. | | |
| 9,513,747 B2 * | 12/2016 | Nakajima | ............... | G06F 3/044 |
| D780,182 S | 2/2017 | Klein et al. | | |
| 2002/0067424 A1 * | 6/2002 | Brunner, Jr. | ............... | B64D 47/08 348/373 |
| 2003/0006223 A1 * | 1/2003 | Davis | ............... | A61B 5/083 219/201 |
| 2003/0043589 A1 * | 3/2003 | Blank | ............... | B60Q 1/2665 362/494 |
| 2004/0165248 A1 * | 8/2004 | Tonar | ............... | B60Q 1/2665 359/265 |
| 2006/0071301 A1 * | 4/2006 | Luo | ............... | G03F 7/091 257/632 |
| 2006/0098289 A1 * | 5/2006 | McCabe | ............... | B60R 1/12 359/603 |
| 2006/0126150 A1 * | 6/2006 | Tonar | ............... | B60Q 1/2665 359/265 |
| 2006/0232972 A1 * | 10/2006 | Mochizuki | ............... | F21V 29/90 362/253 |
| 2009/0207514 A1 * | 8/2009 | McCabe | ............... | G02F 1/157 359/871 |
| 2010/0110523 A1 * | 5/2010 | Varaprasad | ............... | B60R 1/089 359/273 |
| 2010/0309553 A1 * | 12/2010 | Nagamizu | ............... | A61B 1/04 359/512 |
| 2011/0062135 A1 * | 3/2011 | Duchayne | ............... | H05B 3/84 219/201 |
| 2011/0149177 A1 * | 6/2011 | Takata | ............... | B29D 11/00278 348/790 |
| 2011/0155713 A1 * | 6/2011 | Wang | ............... | H05B 3/84 219/203 |
| 2011/0297661 A1 * | 12/2011 | Raghavan | ............... | H05B 3/84 219/203 |
| 2012/0091113 A1 * | 4/2012 | Bennett | ............... | B60J 1/1853 219/203 |
| 2012/0117880 A1 * | 5/2012 | Lahnala | ............... | B60J 1/1853 49/70 |
| 2012/0170119 A1 * | 7/2012 | Chu | ............... | G03B 11/00 359/512 |
| 2013/0034825 A1 | 2/2013 | Phillips et al. | | |
| 2013/0043233 A1 * | 2/2013 | Elser | ............... | H05B 3/84 219/211 |
| 2013/0060086 A1 * | 3/2013 | Talbert | ............... | A61B 1/00006 600/110 |
| 2013/0233842 A1 * | 9/2013 | Pys | ............... | B60J 10/70 219/203 |
| 2013/0249375 A1 * | 9/2013 | Panagotacos | ............... | H05B 33/0803 313/13 |
| 2014/0200406 A1 * | 7/2014 | Bennett | ............... | A61B 1/127 600/109 |
| 2015/0079535 A1 | 3/2015 | Hollenbeck et al. | | |
| 2015/0208910 A1 | 7/2015 | Wang | | |
| 2016/0000332 A1 | 1/2016 | Atiya et al. | | |

FOREIGN PATENT DOCUMENTS

| | | |
|---|---|---|
| JP | S6079608 A | 5/1985 |
| JP | 1998511298 A | 11/1998 |
| JP | 2002-299018 A | 10/2002 |
| JP | 2002291684 | 10/2002 |
| JP | 2007151685 A | 6/2007 |
| JP | 2009183380 | 8/2009 |
| JP | 2010530830 A | 9/2010 |
| WO | 97/14349 | 4/1997 |

OTHER PUBLICATIONS

Japanese Office Action for JP2016-554499 dated Oct. 31, 2017, 6 pages.

Japanese Office Action for JP2016-554499 dated Jul. 3, 2018, with English translation, 8 pages.

* cited by examiner

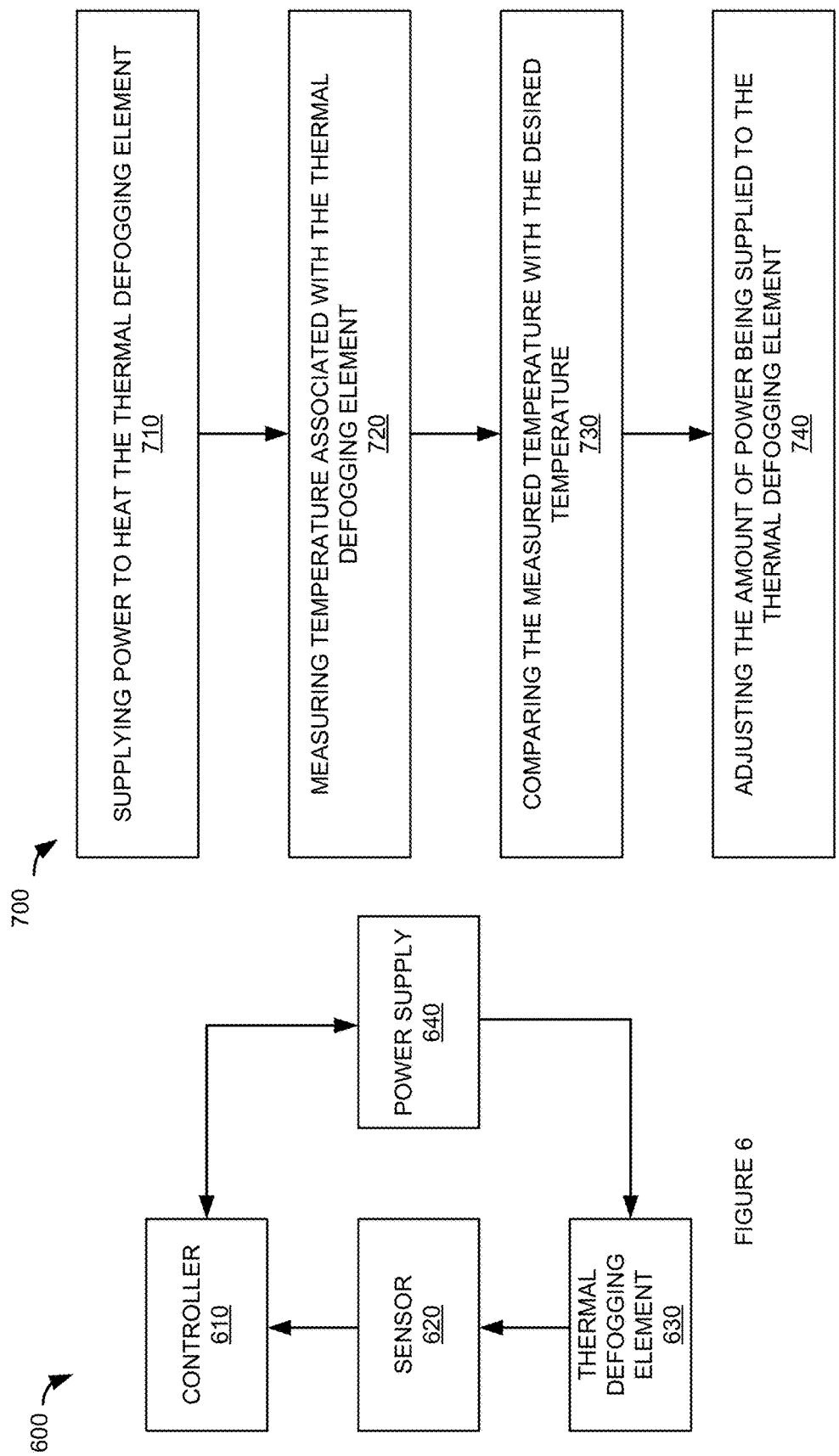

THERMAL DEFOGGING SYSTEM AND METHOD

BACKGROUND

Temperature differences between a patient's body, e.g., oral cavity, stomach cavity, etc., and the surrounding ambient environment may cause condensation to form on a window of a medical device. A medical device may be for example, a scanning device, scope, optical instrument, etc. Condensation may interfere with the optical operation of the medical device. For example, condensation may cause a change in the optical signal (by causing the light to diffract, refract, etc.) that may degrade the optical signal resulting in images with degraded image quality, such as blurry images.

Accordingly, various systems have been developed to defog windows of devices. For example, a fan or an air-pump may be used to blow air to defog the window. The air blown by the fan may or may not be heated. However, for the example where the device is a medical device, using a fan to blow air may cause discomfort due to patient sensitivity, e.g. tooth sensitivity. Further, the addition of a fan increases energy usage, occupies valuable space, and generates noise. In another example system, an opaque foil heater may be used to defog the window of the device. However, the opaque foil heater can degrade the transmission of optical signals. In another example system, the sides of the window of the device may be heated. However, heating the sides of the window may not be sufficient to defog the window as a majority of the heat may dissipate through the ambient environment before reaching the more central portions of the window.

SUMMARY

Accordingly a need has arisen to defog transparent elements or windows of optical devices without substantially degrading the transmission of optical signals and in the case of medical devices, with minimal discomfort to patients. Moreover, a need has arisen to defog windows in the optical footprint (or optical profile) of an optical device while minimally impacting the size and the amount of power the optical device consumes. Furthermore, a need has arisen to defog windows of the optical devices without noise generation.

According to one embodiment, a thermal defogging system may be used to reduce condensation from forming on the transparent elements or windows in an optical device. In one embodiment, the thermal defogging system for an optical instrument is comprised of: at least a primary housing, the primary housing defining an aperture for transmission of optical signals, a transparent element adapted to be aligned with the aperture for transmission of optical signals, at least one side of the transparent element facing the external environment; and a transparent conductive layer covering at least a portion of the transparent element, wherein responsive to the application of electrical power to the transparent conductive layer, the transparent conductive layer generates heat that is thermally communicated to the least one side of the transparent element facing the external environment.

It will become apparent to those skilled in the art after reading the detailed description that the embodiments described herein satisfy the above mentioned needs in addition to other advantages.

BRIEF DESCRIPTION OF DRAWINGS

Embodiments are illustrated by way of example, and not by way of limitation, in the figures of the accompanying drawings and in which like reference numerals refer to similar elements.

FIG. 6 shows a thermal defogging system according to one embodiment.

FIG. 7 shows an exemplary flow diagram of operation of a thermal defogging system according to one embodiment.

DETAILED DESCRIPTION

Figure 1A:
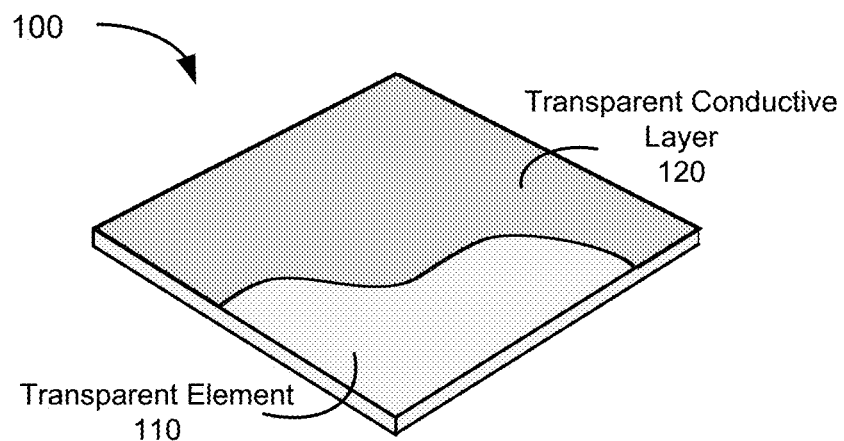
FIG. 1A shows a thermal defogging element in accordance with one embodiment.

References are made in detail to embodiments, examples of which are illustrated in the accompanying drawings. While the embodiments are described in conjunction with the drawings, it is understood that they are not intended to limit the embodiments. The embodiments are intended to cover alternatives, modifications and equivalents. Furthermore, in the detailed description, numerous specific details are set forth in order to provide a thorough understanding. However, it is recognized by one of ordinary skill in the art that the embodiments may be practiced without these specific details. In other instances, known methods, procedures, components, and circuits have not been described in detail as to not obscure aspects of the embodiments. The foregoing description, for purpose of explanation, has been described with reference to specific embodiments. However, the illustrative discussions are not intended to be exhaustive or to limit the invention to the precise forms disclosed. Many modifications and variations are possible in view of the teachings. The implementations described and other implementations are within the scope of the following claims.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of operations or steps or instructions leading to a desired result. The operations or steps are those utilizing physical manipulations of physical quantities. Usually, although not necessarily, these quantities take the form of electrical or magnetic signals capable of being stored, transferred, combined, compared, and otherwise manipulated in a computer system or computing device. It has proven convenient at times, principally for reasons of common usage, to refer to these signals as transactions, bits, values, elements, symbols, characters, samples, pixels, or the like. It should be borne in mind that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "supplying," "measuring," "comparing," "generating," "storing," "adjusting," "transmitting," "receiving," "providing," "accessing," or the like, refer to actions and processes of a computer system or similar electronic computing device or processor. The computer system or similar electronic computing device manipulates and transforms data represented as physical (electronic) quantities within the computer system memories, registers or other such information storage, transmission or display devices.

A thermal defogging system and method for an optical instrument is described. In one embodiment, the thermal defogging system for an optical instrument is comprised of: at least a primary housing, the primary housing defining an aperture for transmission of optical signals, a transparent element adapted to be aligned with the aperture for transmission of optical signals, at least one side of the transparent element facing the external environment; and a transparent conductive layer covering an area at least as large as the optical footprint of the transmitted optical signal through the transparent element, wherein responsive to the application of electrical power to the transparent conductive layer, the transparent conductive layer generates heat that is thermally communicated to the least one side of the transparent element facing the external environment.

In one embodiment, the thermal defogging system includes a thermal defogging element 100 comprised of a transparent element 110 (a transparent substrate) that is coated with a transparent conductive layer 120. According to one embodiment, the thermal defogging element 100 may be aligned to an aperture of a device, e.g., scanning device, scope, optical instrument, etc. The thermal defogging element heats up to a predetermined set temperature in response to receiving electrical power, thereby removing condensation. The condensation may result from humidity from patient's internal cavity and a temperature difference between the ambient temperature and the temperature of patient's internal cavity. The patient's internal cavity may include oral cavity, stomach cavity, etc.

It is appreciated that the thermal defogging element may be integrated within a housing of the device. In one embodiment, the thermal defogging element is integrated into the device housing and is not removable during ordinary use. In an alternative embodiment, the thermal defogging element may be removable, thereby allowing it to be disinfected after use. In another embodiment, the thermal defogging element may be removable and disposable such that it can be replaced with a new thermal defogging element after use with each patient.

The thermal defogging system includes at least a primary housing that houses the optical instrument. In one example, the defogging system also includes a secondary housing that physically surrounds the primary housing. It is appreciated that according to various embodiments, the thermal defogging element may be isolated from a patient's body, e.g., oral cavity, by the secondary housing. In one example, the secondary housing prevents contact between the thermal defogging element and the patient's body and allows the thermal defogging element to be reused without a need to disinfect and/or replace the thermal defogging element.

It is appreciated that for illustration purposes, various embodiments are described in relation to medical devices and defogging of the transparent elements or transparent windows associated therewith. However, the specifics discussed are merely illustrative in nature and are not intended to be limited by the scope of the embodiments. For example, embodiments described herein are equally applicable to other types of devices where defogging of a window is required. It is appreciated that for illustration purposes, various embodiments are described in relation to oral cavities and temperatures associated therewith. However, the specifics discussed are merely illustrative in nature and are not intended to limit the scope of the embodiments. For example, embodiments described herein are equally applicable to other medical devices used for other body cavities such as the stomach cavity during surgery, etc.

Referring now to FIG. 1A shows a thermal defogging element 100 in accordance with one embodiment. In the embodiment shown, the thermal defogging element 100 is comprised of a transparent element 110 (or substrate) and a transparent conductive layer 120. The thermal defogging element has high optical transmission properties, e.g., greater than 90%, greater than 97%, etc. In one example, the transparent conductive layer covers an area at least as large as the optical footprint of the transmitted optical signals through the transparent element. In one embodiment, the transparent conductive layer 120 coats or is formed on the surface of the transparent element 110. It is appreciated that the transparent element and the transparent conductive layer 120 are both transparent. It is further appreciated that transparent layers, transparent conductive layers, transparent elements or substrates, as used throughout the detailed description, refer to material that have high optical transmission properties, e.g., at least 90%, at least 97%, etc. transmissibility properties. It is noted that terms thermal defogging element and defogging element are used interchangeably throughout this detailed description. According to one embodiment, the transparent element 110 is a glass substrate. However in various embodiments, other transparent substrates may be used. For example, the transparent element 110 may be comprised of a transparent plastic or a transparent polycarbonate material. The thickness of the transparent element 110 may vary depending on application. For example, in one embodiment the thickness of the transparent substrate 110 may be between 0.75 mm to 1 mm. As previously stated, in one embodiment the thermal defogging element 100 includes a transparent element 110 that is coated with a transparent conductive layer 120. In one exemplary embodiment, the conductive layer 120 is a very thin submicron layer comprised of a material that when power is applied, generates heat, such as an electrically resistive layer. In one example, the transparent conductive layer is a thin layer of a metal compound such as indium tin oxide. According to some embodiments, a conductive layer 120 other than indium tin oxide may also be used. For example, a fluorine tin oxide, an aluminum tin oxide or gold layer may similarly be used. As such, references to indium tin oxide are merely exemplary and not intended to limit the scope of the embodiments described herein. The transparent conductive layer 120 may be applied to the transparent substrate 110 using different processes. In an alternative embodiment, the conductive material (for example, indium tin oxide) is scattered over the transparent substrate 110. In one example, the transparent conductive layer 120 is applied and the thickness precisely controlled by a deposition process.

According to one embodiment, the transparent conductive layer 120, which is deposited over the transparent element 110 has an electrical resistance. This electrical resistance causes the transparent conductive layer 120 to heat up once a specific voltage value is applied to it. This voltage is also known as an activation voltage. The resistance of the transparent conductive layer 120 may be measured in ohms per square unit. As such, the length (for example as shown in FIG. 1C) of the transparent element 110 that the conductive layer 120 is deposited over proportionally impacts the resistance of the conductive layer 120. Also, the resistance value is inversely impacted by the width (shown in FIG. 1C) of the transparent element 110. According to one embodiment, a uniform heat flux is generated by the thermal defogging element 100 if the length of the thermal defogging element 100 does not vary with respect to the electrical connections (electrical bars 160 shown in FIG. 1C). In other words, the geometry of the thermal defogging element 100 determines whether a uniform or non-uniform heat flux is generated by the thermal defogging element 100.

In one embodiment, the transparent conductive layer 120 may be further coated with a dielectric insulating layer (not shown), thereby protecting the transparent conductive layer 120. In the embodiment where a dielectric insulating layer is deposited over the transparent conductive layer, the dielectric layer can act as a protective coating to prevent the transparent conductive layer from wearing off or being damaged during use. The protective function of the dielectric insulation layer can be helpful because the transparent conductive layer can be very thin (micro-millimeters) and can be easily damaged. In addition to a protective function, the dielectric insulating layer can provide an insulating function, thus preventing the conductive layer from making electrical shorts with surrounding conductive objects. The dielectric insulating layer may further be used for optical index matching the conductive layer 120 to the surrounding ambient environment, e.g., air, body cavity, etc. In addition, the dielectric insulation layer may be a non-glare layer that the transparent conductive layer 120 may be coated with to create an anti-reflective coating.

Figure 1B:
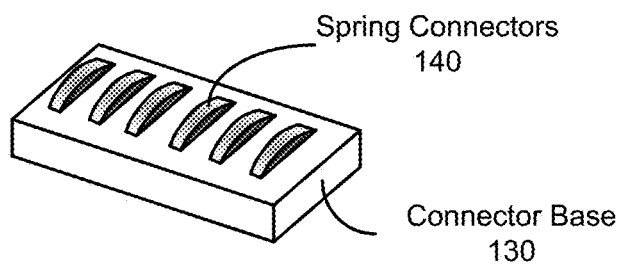
FIG. 1B shows an exemplary electrical connection in accordance with one embodiment.
Figure 1C:
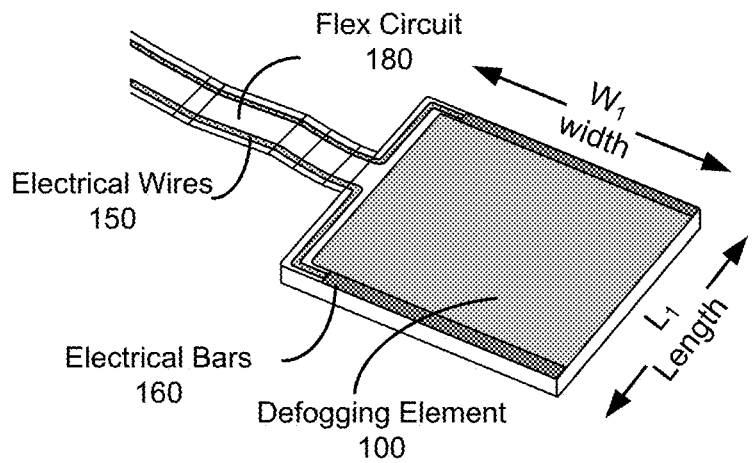
FIG. 1C shows a thermal defogging element with an electrical connection in accordance with one alternative embodiment.

Referring now to FIG. 1B, an exemplary electrical connection in accordance with one embodiment is shown. Modular contacts may be used to supply power to the thermal defogging element. For example, the modular contacts may include spring type connectors 140 positioned over a connector base 130 to make electrical connection to the conductive layer 120. It is appreciated that the spring type connectors 140 contract and expand accordingly to grip the thermal defogging element and make electrical contact with the conductive layer 120. Accordingly, once power is supplied via the spring type connectors 140, the thermal defogging element becomes operational and its conductive layer 120 heats up, thereby removing condensation. It is appreciated that other types of electrical connections may be used, as discussed below.

Referring now to FIG. 1C, a thermal defogging element with an electrical connection in accordance with one alternative embodiment is shown. A thermal defogging element 100 is substantially similar to the thermal defogging element 100 discussed with respect to FIG. 1A. In this embodiment, power may be provided to the thermal defogging element 100 via a flex circuit 180. The flex circuit 180 may include electrical wires 150 for conducting electricity and power to the thermal defogging element 100. The electrical wires 150 provide power to electrical bars 160 that are in contact with the transparent conductive layer 120 of the thermal defogging element 100. The electrical bars 160 may also be referred to as bus bars. The electrical bars 160 may make electrical contact with the transparent conductive layer 120 by being soldered, printed, deposited, glued, or scattered over the conductive coating layer 120. In an embodiment where a dielectric insulation layer is deposited over the transparent conductive layer 120, the electrical bars 160 may be disposed on the dielectric insulation layer and penetrate the dielectric layer to provide an electrical connection to the conductive layer 120. In various embodiments, the electrical bars 160 may be glued to the transparent conductive layer 120 using, for example, electrically conductive glue. It is appreciated that an electrically conductive adhesive or foam over the electrical bars 160 and wires embedded inside the adhesive may also make the electrical connection between the electrical bars 160 and the electrical power source. In the embodiment shown in FIG. 1C, two electrical bars 160 are shown parallel to one another. As such, uniformly coating the transparent substrate 110 with the conductive coating layer 120 causes the heat flux to be generated uniformly throughout the surface. It is appreciated that using two electrical bars 160 is merely exemplary and not intended to limit the scope of the embodiments. For example, embodiments may include one or more electrical bars, various other electrically conductive shapes and/or materials, non-parallel electrically conductive bars, etc. Furthermore, it is appreciated that the thermal defogging element 100 may be shaped based on the shape of the aperture formed in the housing of the device. For example, the thermal defogging element 100 may be rectangular, square, elliptical, circular, etc., based on the aperture of the device.

Figure 1D:
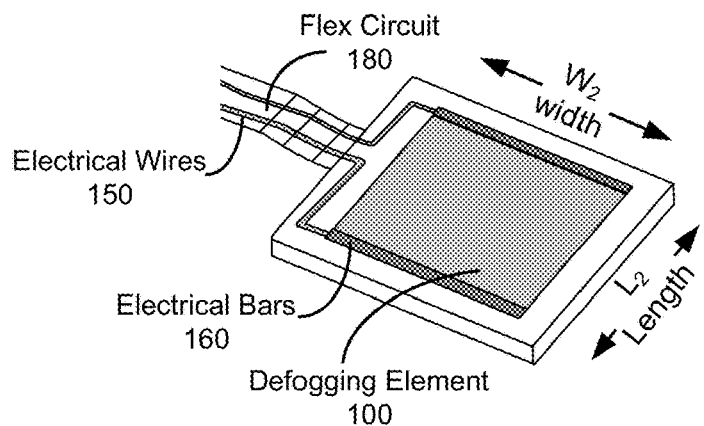
FIG. 1D shows a thermal defogging element with an electrical connection in accordance with one alternative embodiment.

As previously stated, the thermal defogging element 100 shape may be on the shape of the aperture of the device. In one example, the shape of the aperture may be smaller than the transparent element. In one embodiment shown in FIG. 1D, the shape of the transparent conductive layer 120 of the thermal defogging element 100 matches the shape of the aperture of the defogging element housing. The embodiment shown in FIG. 1D is similar to the embodiment shown in FIG. 1C. However, in FIG. 1D, instead of extending over substantially the entire substrate (to the edge or substantially to the edge of the transparent element as shown in FIG. 1C), the transparent conductive layer 120 extends only across a limited portion of the transparent element—an area that mirrors the size of the aperture.

Figure 1E:
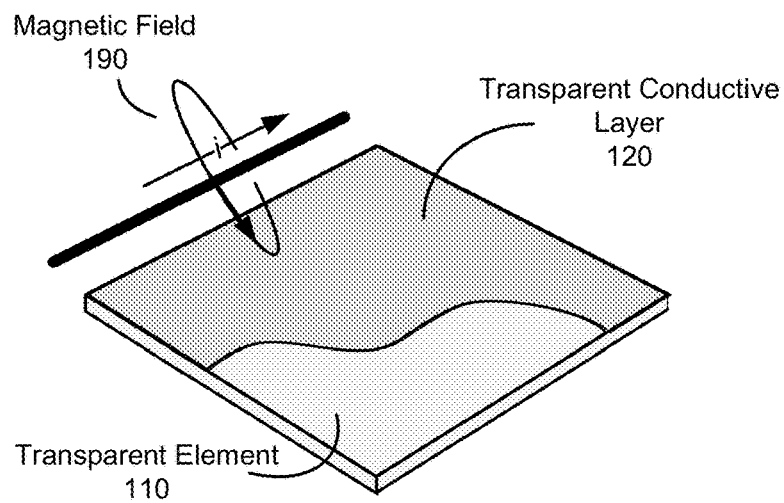
FIG. 1E shows a magnetically activated thermal defogging element in accordance with one embodiment.

For purposes of discussion, assume that the transparent element 110 shown in FIG. 1C is identical to the transparent element 110 shown in FIG. 1D. The area of the transparent conductive layer shown in FIG. 1C is equal to $L_1$ multiplied by $W_1$. However, although the length and width of the substrate over which the conductive layer is deposited are the same, the transparent conductive layer shown in FIG. 1D is smaller in area than the electrically conductive layer shown in FIG. 1D. In the example shown in FIG. 1D, the area of the transparent conductive layer 120 is equal to length $L_2$ multiplied by a width $W_2$, where $L_2<L_1$ and where $W_2<W_1$. Referring now to FIG. 1E, a magnetically activated thermal defogging element in accordance with one embodiment is shown. Power may be provided, by various means, to the thermal defogging element 100 in order to heat up the thermal defogging element 100. For example, instead of providing an electrical connection, as shown in FIGS. 1B-1D, a magnetic field 190 may provide the necessary energy. As such, the magnetic field 190 may cause the transparent conductive layer 120 of the thermal defogging element to heat up. In this example, magnetic field 190 may be provided using a wire carrying current that is positioned in close proximity to the thermal defogging element. It is appreciated that the magnetic field may be provided using other means, e.g., using a stator assembly, coil, etc. According to one embodiment, a magnetic field may be used to induce an Eddy current on the conductive coating layer 120 of the thermal defogging element 100 causing it to heat up. In embodiments where power is provided using a magnetic field 190, electrical connections as discussed with respect to FIGS. 1B, 1C and 1D may be eliminated. Therefore, it is appreciated that power may be provided to the thermal defogging element using other means. Further examples may include the conductive coating layer 120 having chemical compounds that heat up in response to receiving light with certain wavelength, e.g., ultraviolet, etc. As such, the thermal defogging element may heats up in the presence of light of a certain wavelength of light.

Figure 1F:
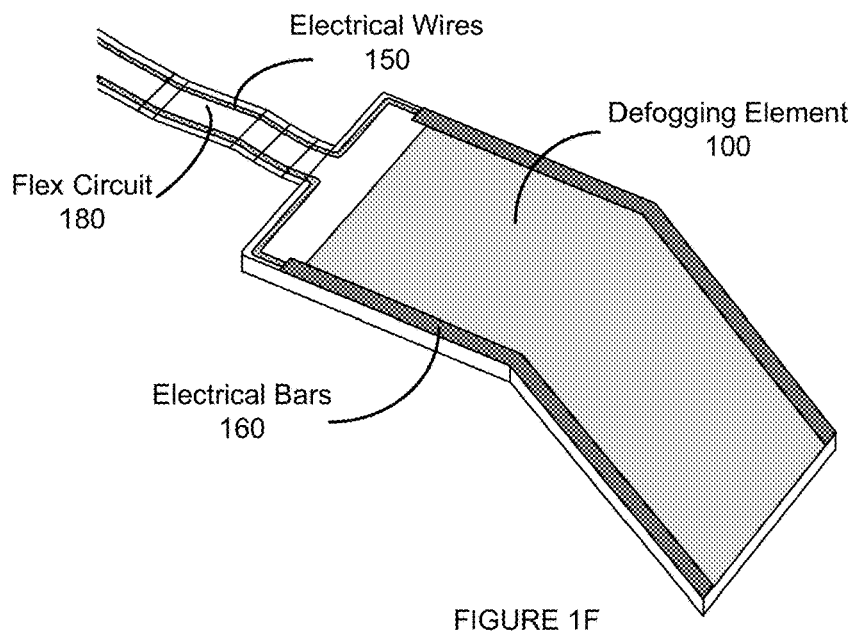
FIGS. 1F-1I show exemplary thermal defogging elements according to various embodiments.

Referring now to FIGS. 1F-1I, exemplary thermal defogging elements according to various embodiments are shown. FIG. 1F shows a thermal defogging element with a flex circuit 180 having electrical wires 150, electrical bars 160, and a defogging element 100 that are similar to those as described in FIG. 1C. In the embodiment shown in FIG. 1F, however, a first region of the defogging element 100 and the electrical bars 160 are inclined at an angle somewhere between 0 degrees and 180 degrees with respect to at second region of the defogging element. For example, the first region of the defogging element 100 and the electrical bars 160 may be angled at midpoint, a quarter point, three quarter point, etc. with respect to a second region of the thermal defogging element. In this non-limiting embodiment, the two electrical bars 160 are shown parallel to one another. As such, uniform heat flux may be generated by uniformly coating the transparent element 110 with the transparent conductive layer 120 along with the two electrical bars 160 that are equidistant from one another.

Figure 1G:
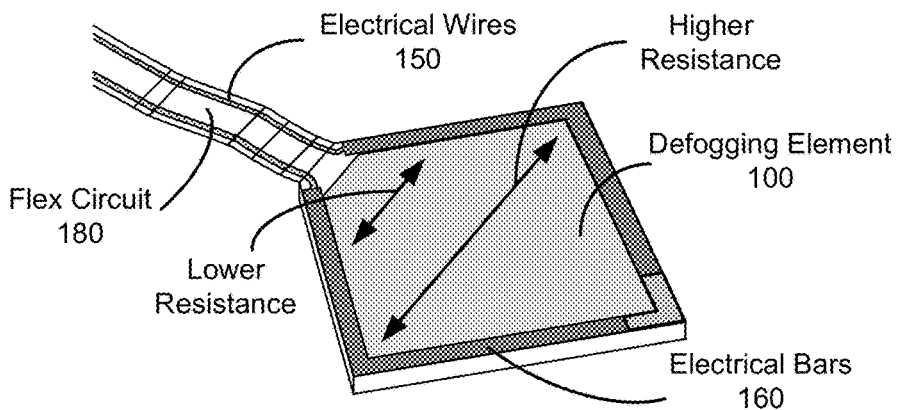
Figure 1H:
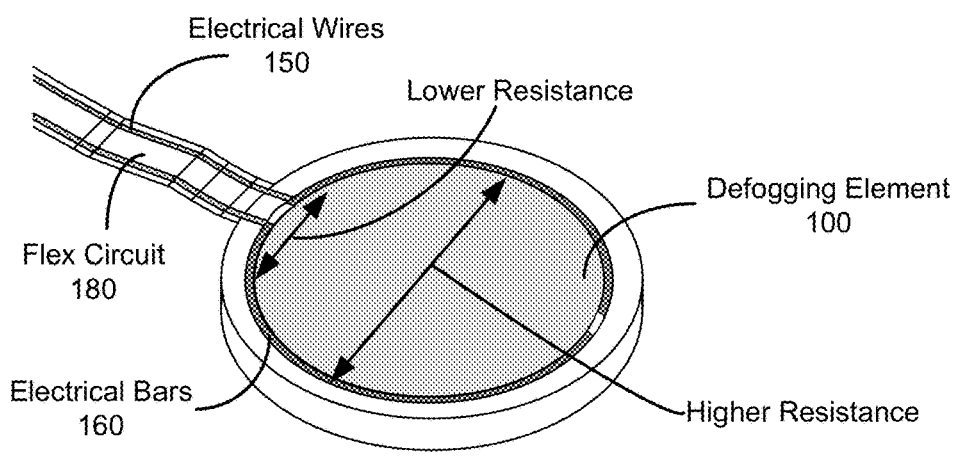
Figure 1I:
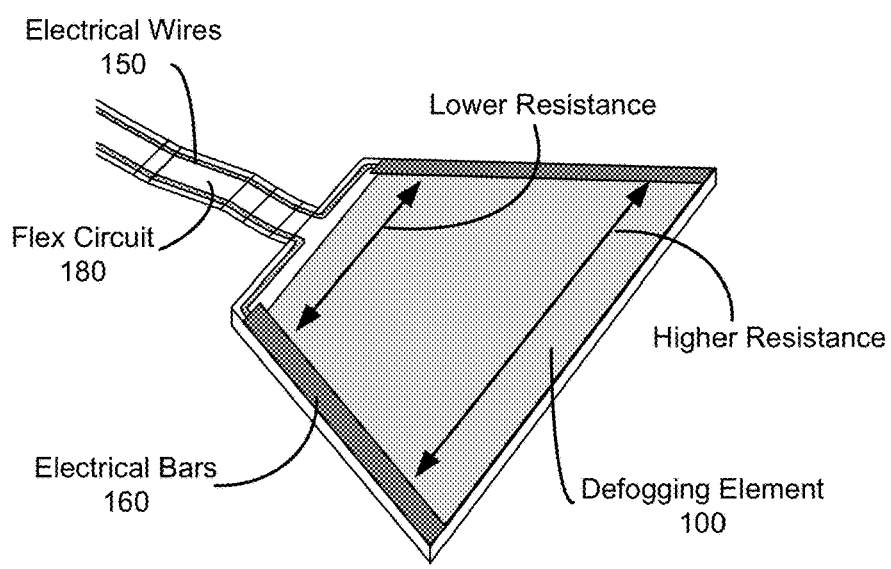

Referring now to FIGS. 1G-1I, exemplary thermal defogging elements according to various embodiments are shown. In these embodiments, the flex circuits 180, the electrical wires 150, the electrical bars 160, and the defogging elements 100 operate substantially similar to those described above. However, in the embodiments shown in FIGS. 1G-1I, the electrical bars 160 and the thermal defogging elements 100 are shaped differently based on the window aperture of the device. Any shape may be used including, for example, square, round, triangle, diamond, trapezoid, hexagon, rectangle, oval, etc. According to some embodiments, a non-uniform heat flux generation may be desired. Non-uniform heat flux may be generated using non-equidistant electrical bars, as shown in FIGS. 1G1I.

In some embodiments, uniform heat flux may be generated despite a non-uniform structure of the thermal defogging element. For example, the transparent conductive layer 120 of the thermal defogging element may be deposited non-uniformly based on shape and location of the electrical bars in order to generate heat uniformly. The resistance of the transparent conductive layer 120 is based on the length of the conductive material between the electrical bars, i.e. a higher path length has a higher resistance. For example referring to FIG. 1I, the path labeled "Lower Resistance" has a lower resistance value than the path labeled "Higher Resistance" as the path labeled "Lower Resistance" is shorter in length. Thus in one example, a thinner conductive material layer may be deposited over a region of the thermal defogging element where the electrical bars are closer together in comparison to other regions to generate a uniform heat flux. As such, the resistance of the region where the electrical bars are closer together is increased to substantially match the resistance of other regions in order to generate a uniform heat flux.

Figure 2A:
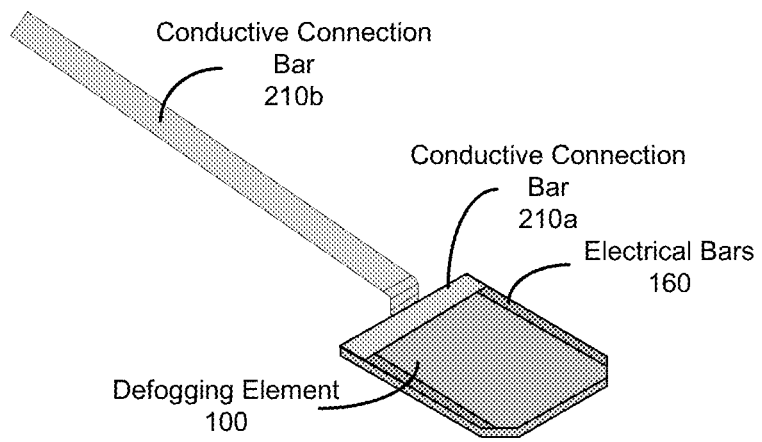
FIGS. 2A-2D show components of a thermal defogging system according to one embodiment.

FIGS. 2A-2D shows parts of a thermal defogging system for an optical instrument or device according to one embodiment. Referring to FIG. 2A shows a thermal defogging element (comprised of a transparent element 110 and a transparent conductive layer 120) and its corresponding electrical connections according to one embodiment. The thermal defogging element is similar to the thermal defogging element and electrical connections shown in FIGS. 1A, 1C-1D and 1F-1I. For example, comparing FIG. 2A to FIG. 1C, the electrical wires 150, electrical bars 160 and flex circuit 180 shown in FIG. 1C provides similar functionality and support as the electrical bars 160 and conductive connection bar 210*a-b* shown in FIG. 2A. In one example, a first region of the conductive connection bar 210*a* electrically connects the electrical bars 160 to second region of the conductive connection bar 210*b*. The second region of the conductive connection bar 210*b* connects the first region of the conductive connection bar 210*a* to a power source (not shown).

Figure 2B:
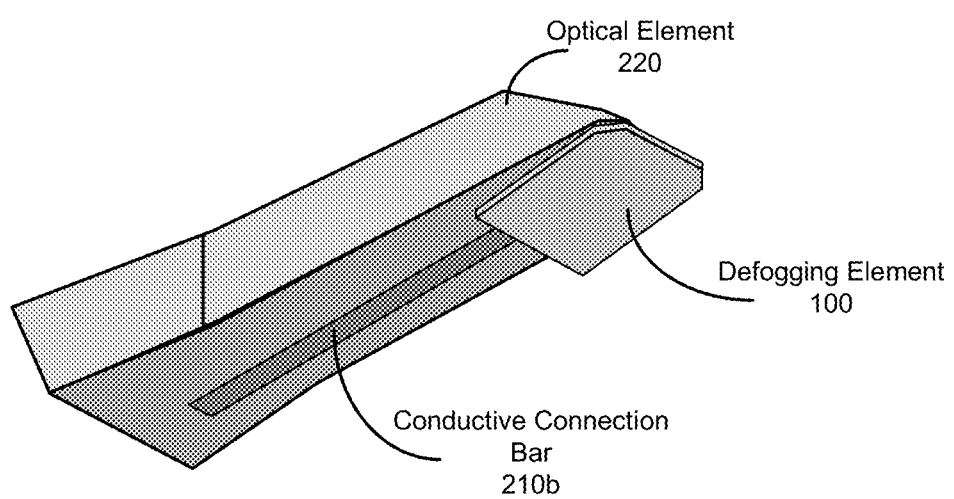
Figure 2C:
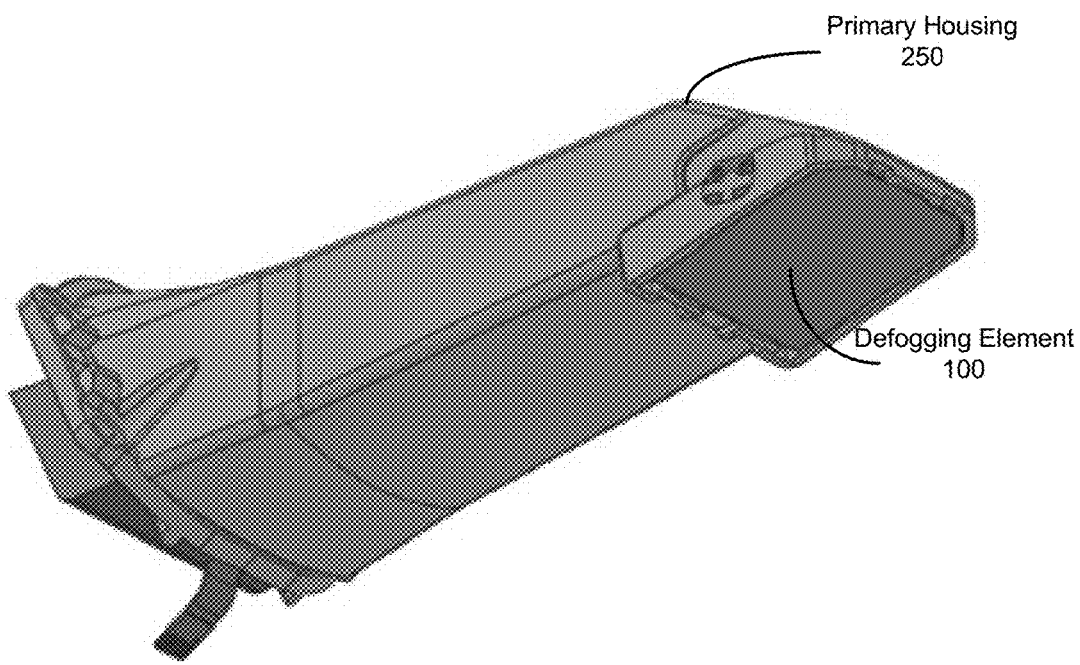

Referring to FIG. 2B shows an optical element (a prism) 220 of the optical device in position next to the thermal defogging element 100 before insertion of the optical element 220 and thermal defogging element 100 into the primary housing. The embodiment shown in FIG. 2C shows a view of the thermal defogging system after insertion of the thermal defogging element 100 and the optical element 220 inside of the primary housing. As previously stated, in one example the thermal defogging system includes at least a primary housing 250. In the embodiment shown in FIG. 2C, the primary housing 250 is also the housing of the optical device (the optical device housing). In the embodiment shown in FIG. 2C, the primary housing is a support structure responsible for maintaining the position of the thermal defogging element 100 so that it is aligned with the optical footprint of the transmitted optical signals from the optical element. In addition, the primary housing defines an aperture for transmission of optical signals from the optical prism 220 (inside of the optical device) to an area external to the primary housing (i.e. the patient cavity).

In the embodiment shown in FIG. 2C, the primary housing 250 supports the defogging element 100 and positions it so the defogging element 100 is aligned with the aperture of the primary housing. At least one side of the transparent element of the defogging element 100 (transparent element 110 coated with a transparent conductive layer 120) faces the external environment, the external surface 234 in FIG. 2D of the defogging element. Responsive to the application of electrical power to the transparent conductive layer, the transparent conductive layer of the defogging element 100 generates heat that is thermally communicated to the at least one side of the defogging element facing the external environment. In one embodiment, the transparent conductive layer of the defogging element 100 is at least as large as the optical footprint generated by the optical instrument. In one example, the portion of the transparent element that the transparent conductive layer extends over matches the shape of the aperture formed by the primary housing.

In one embodiment, the external surface 234 of the defogging element 100 is coated with a transparent conductive layer 120 and when power is applied to the transparent conductive layer, the heat generated is sufficient to prevent condensation from forming on the external surface of thermal defogging element so that the defogging element 100 (the window of the optical device) maintains its high optical transmission properties. In an alternative embodiment, the internal surface 232 of the defogging element 100 is coated with the transparent conductive layer 120 and responsive to the application of power, the internal surface 232 of the defogging element 100 is heated. In this example, the heat generated on the internal surface of the defogging element is thermally communicated from the internal surface 232 of the defogging element through the transparent element to the external surface 234 of the defogging element that faces the external environment. In one embodiment, heat is thermally transmitted or communicated for example, by convection or conduction. For the example of a medical optical instrument, the heat transmitted to the external surface of the defogging element should be sufficient to prevent condensation from forming on the external surface of the defogging element when positioned inside a patient's cavity. In one example, the transparent element 110 of the defogging element is glass. Although glass is not a particularly efficient heat transmitter, the glass may be made sufficiently thin to transmit the heat required to prevent condensation from forming on the external surface of the defogging element.

In the embodiment shown in FIG. 2C, it is appreciated that in this embodiment, the shape of the head of the optical device that is inserted into the patient cavity, the optical device wand head, is trapezoidal in shape. However, it is appreciated that the trapezoidal shape of the wand head is exemplary and should not be construed to limit the scope of the embodiment. For example, the wand head may be rectangular in shape. It is further appreciated that although the defogging element is shown positioned within an optical device head that is located at the end of the wand, in other embodiments the defogging element may be positioned at an alternative location within the optical device, displaced some predetermined distance from the end of the wand.

Figure 2D:
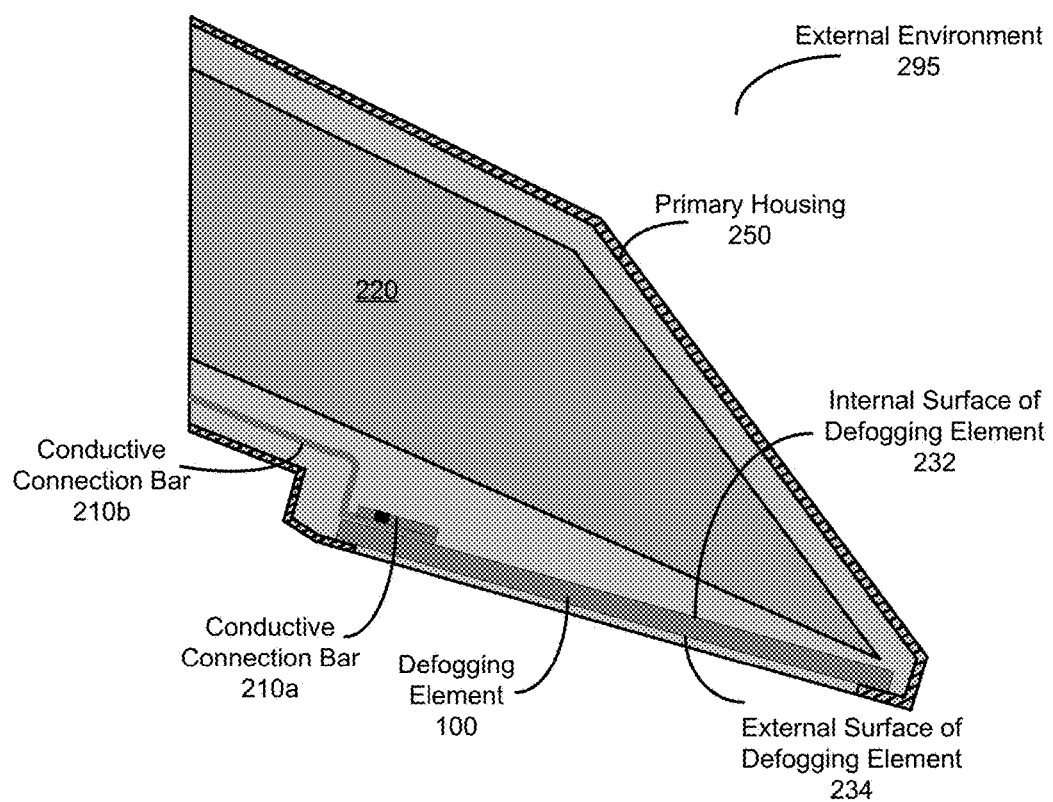

FIG. 2D shows a cross-sectional view of the optical device and defogging system shown in FIG. 2C. In one embodiment, the thermal defogging system for an optical device is comprised of: at least a primary housing, the primary housing defining an aperture for transmission of optical signals, a transparent element adapted to be aligned with the aperture for transmission of optical signals, at least one side of the transparent element facing the external environment; and a transparent conductive layer covering an area at least as large as the optical footprint of the transmitted optical signal through the transparent element, wherein responsive to the application of electrical power to the transparent conductive layer, the transparent conductive layer generates heat that is thermally communicated to the least one side of the transparent element facing the external environment.

Referring to FIGS. 2C and 2D, the thermal defogging system is comprised of at least a primary housing 250, where the primary housing 250 defines an aperture for transmission of optical signals. Referring to the embodiment shown in FIGS. 2C and 2D, the aperture is the portion of the housing that surrounds the defogging element. The aperture creates an opening that the optical signals from the optical element 220 can transmit optical signals through. The transparent element 110 of the defogging element 100 is adapted to be aligned with the aperture of the primary housing for transmission of optical signals. At least one side 234 of the transparent element faces the external environment 295. In one example, the transparent conductive layer of the defogging element 100 covers an area at least as large as the optical footprint of the transmitted optical signal through the transparent element. When electrical power is applied to the transparent conductive layer, the transparent conductive layer of the defogging element 100 generates heat that is thermally communicated to the at least one side of the transparent element facing the external environment.

The transparent conductive layer covers at least a portion of the transparent element. In one example, the transparent conductive layer covers all or substantially all of the surface of the transparent element. As previously stated, in one example the transparent conductive layer of the defogging element 100 covers an area at least as large as the optical footprint of the transmitted optical signal through the transparent element. In an alternative example (for example where the aperture defined by the primary housing is smaller than the optical footprint), then the transparent conductive layer may be the size of the aperture of the primary housing. In one example, the conductive film has an annular share over the entire optical footprint or a portion of the optical footprint of the transmitted optical signal. In alternative examples, the area that the transparent conductive film covers may be an area that is only be a portion of the optical footprint. However, the area of the transparent conductive film should be sufficient to generate enough heat to defog the at least one side of the transparent element facing the external environment along the optical footprint of the transmitted signal.

In one embodiment, the primary housing 250 supporting and aligning the thermal defogging element to the aperture of the primary housing is designed to be permanently mechanically coupled to the thermal defogging element and thus the thermal defogging element is not easily removable. For example, for the optical device shown in FIG. 2D—the thermal defogging element 100 can be removed from inside of the primary housing however, not without physically separating of the thermal defogging element from the primary housing and not without making the optical device non-functioning. In an alternative implementation (not shown), electrical connection of the thermal defogging element 100 can be made to optical device via electrical connectors that are externally accessible. For example, spring connectors similar to those shown in FIG. 1B could be positioned on the internal surface of the trapezoidal wand head such that the defogging element could be inserted into the spring contacts for providing an electrical connection from outside of the primary housing. This would allow the thermal defogging element to be easily removable for replacement or alternatively easily available to be disinfected after patient use. However, even with the removability of the thermal defogging element, the primary housing would still need to be disinfected after each use in the event of patient contact.

When a medical device having the configuration shown in FIG. 2C enters for example, the oral cavity of a patient, it is likely that the device may come into contact with the patient. Thus the embodiment shown in FIG. 2C will need to be disinfected after each use. Instead of disinfecting the optical instrument after each use, it may be desirable to provide a barrier between the optical instrument and the patient cavity into which the optical instrument may be inserted. In the embodiment shown in FIGS. 3A-3C and FIGS. 4A-4C, a physical barrier is placed between the patient and the optical instrument, so that the optical instrument and/or the defogging element of the optical instrument may not need to be disinfected after each use.

Figure 3A:
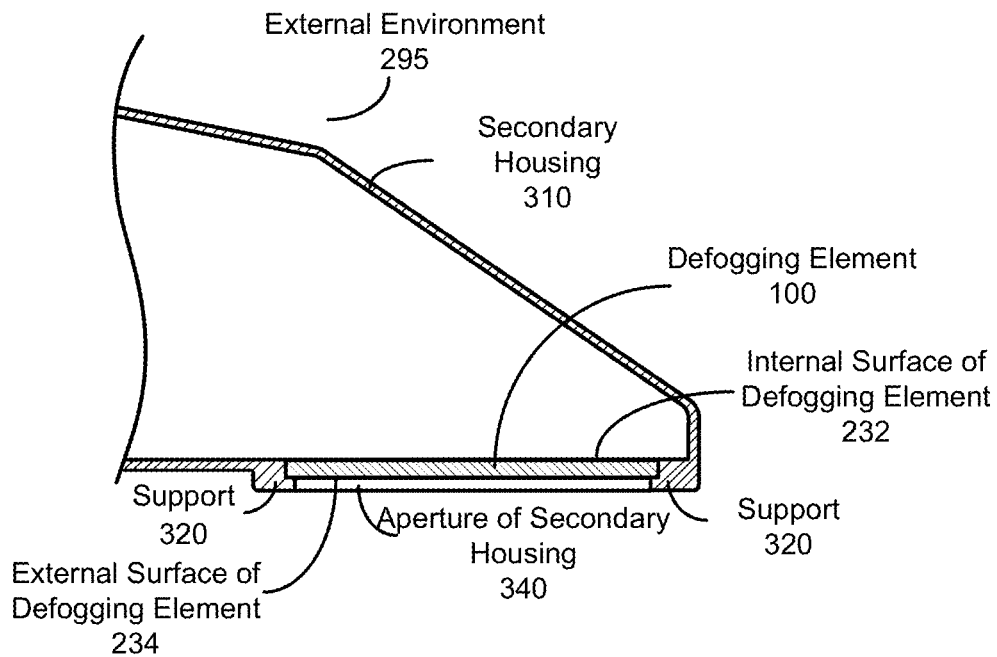
FIGS. 3A-3C show a device with a thermal defogging system according to an alternative embodiment.
Figure 3B:
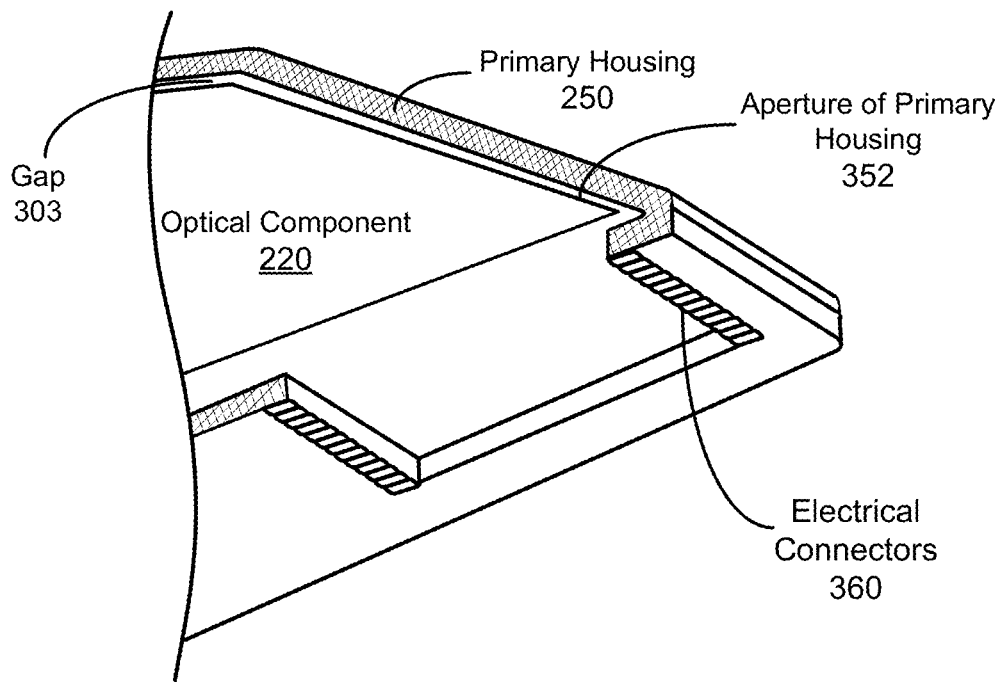
Figure 3C:
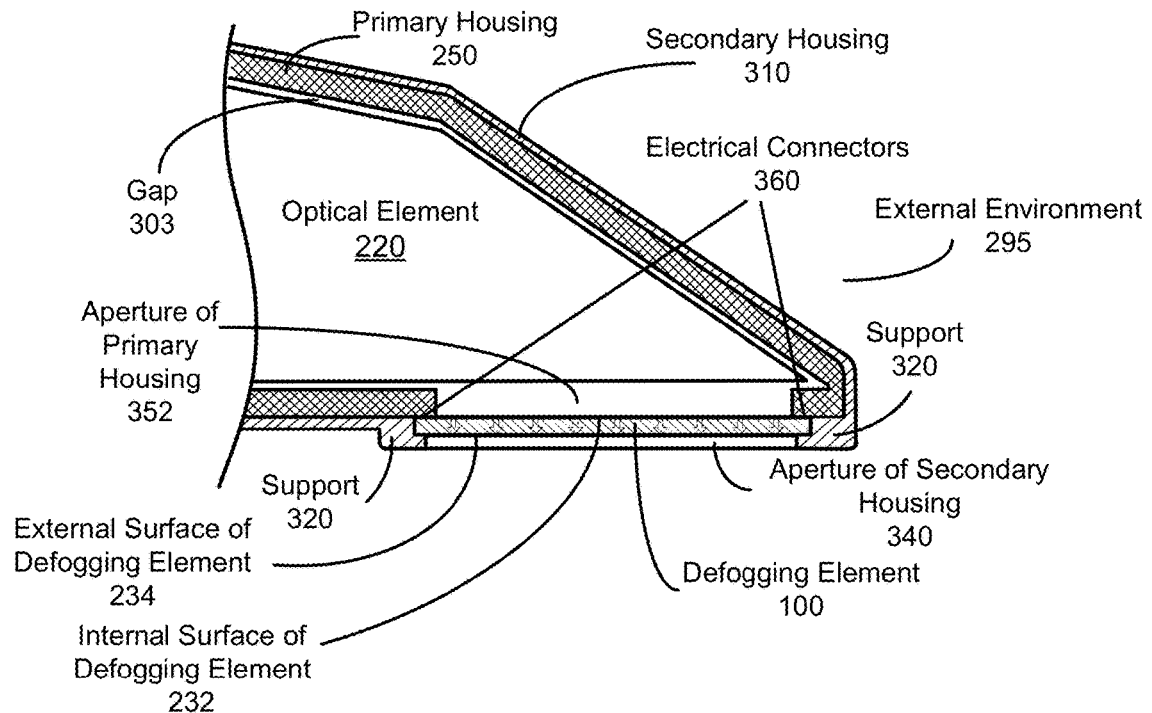

Referring now to FIGS. 3A-3C, shows parts of a thermal defogging system according to one embodiment. The embodiment shown in FIGS. 3A-3C is similar to the embodiment shown in FIGS. 2A-2D, except that the embodiment shown in FIGS. 3A-3C in addition a primary housing—the thermal defogging system also includes a secondary housing. Comparing the implementation shown in FIGS. 2A-2D to FIGS. 3A-3C—in additional change is that instead of the thermal defogging element 100 being supported by the primary housing, the thermal defogging element 100 is supported by and integrated into the secondary housing. In one embodiment the secondary housing may be removable.

In the embodiment shown in FIGS. 3A-3C, the secondary housing is an external sleeve that protects the optical instrument from contact with, for example, the patient's oral cavity. In the embodiment shown in FIGS. 3A-3C, the defogging element 100 (the transparent element and the transparent electrically conductive layer) is supported by and positioned within the secondary housing. Referring to FIG. 3A shows a secondary housing 310 that acts as an external sleeve to protect the optical instrument or medical device from contact with the patient cavity. FIG. 3B shows the primary housing 250 of the optical instrument in accordance with one embodiment. FIG. 3C shows coupling of the secondary housing 310 with the primary housing 250 in accordance with one embodiment. Referring to FIG. 3A, the thermal defogging system includes a secondary housing 310 that prevents fluids and other contaminants from reaching the primary housing 250 of the device (shown in FIGS. 3B and 3C). According to one embodiment, the secondary housing 310 may be removable. For example, the secondary housing 310 may be removed and disinfected after use with each patient. Alternatively, the secondary housing 310 may be disposable and replaced after use with each patient. In one example, the secondary housing may be made of plastic or another inexpensive material. Further, in one embodiment, the defogging element 100 may be removable from the secondary housing 310. As such, the defogging element 100 may be removed and disinfected between patients. Alternatively, the defogging element 100 may be disposable and replaced after use with each patient.

Referring now to FIG. 3A, the defogging system includes a secondary housing 310 that supports a defogging element 100. The defogging element 100 is similar to the thermal defogging elements previously discussed. In the embodiment shown in FIGS. 2A-2D, it is the primary housing 250 that supports the defogging element. In the embodiment shown in FIGS. 2A-2D both the external surface of the primary housing and the external surface 234 of the defogging element face the external environment. In the embodiment shown in FIGS. 3A-3C, it is the secondary housing 310 (that supports the defogging element 100) and the external side 234 of the defogging element are in contact with the external environment 295—while the primary housing that is enclosed within the secondary housing is not directly in contact with the external environment. The secondary housing 310 includes supports 320 that hold the defogging element 100 in place so that the transparent element of the defogging element is aligned with the window aperture of the primary housing.

In the embodiment shown in FIG. 3A, an aperture 340 is formed in the secondary housing. When as shown in FIG. 3C, the primary and secondary housing are coupled together, optical signals travel from the optical prism 220 to the aperture of the primary housing (element 252 shown in FIG. 3B) through the defogging element 100 through the aperture 340 of the secondary housing to the external environment 295 (i.e. the patient's body cavity, e.g., oral cavity, stomach cavity, etc.

It is appreciated that the defogging element 100 that is housed within the secondary housing 310 is positioned to align with the aperture 352 of the primary housing. The defogging element 100, by virtue of its transparency, allows unaltered optical signals to travel between the patient's body cavity and the medical device. The surface of the defogging element 100 facing the aperture of the primary housing (after the primary housing is positioned inside the secondary housing) is referred to as the internal surface of the defogging element 232. The surface of the defogging element 100 facing the external environment 295 is referred to as the external surface of defogging element 234. In the embodiment shown in FIGS. 3A-3C, the defogging element is comprised of a transparent element that is coated with a transparent conductive layer. At least one side of the transparent element faces the external environment 295. In one embodiment, the transparent conductive layer coating is on the external surface of the defogging element 234. In an alternative embodiment, the transparent conductive layer is on the internal surface of the defogging element 232. In either embodiment, the transparent conductive layer generates heat that is thermally communicated to the side of the transparent element facing the external environment.

While the defogging element 100 shown in FIG. 3A is shown in a horizontal position or configuration, various embodiments may not be limited to such configurations. For example, the defogging element 100 may be positioned such that it is at an angle with respect to the horizontal plane. Positioning the defogging element 100 in a horizontal configuration or at an angle may provide the defogging element 100 certain properties. For example, changing the angle of the defogging element 100 with respect to the horizontal plane may affect refracting properties, reflecting properties, light index matching properties, etc.

Referring now to FIG. 3A shows a secondary housing 310 that supports a defogging element 100. A thermal defogging system and method for an optical instrument is described. The thermal defogging system is comprised of: a defogging element housing, the defogging element housing comprising at least a primary housing, the primary housing defining an aperture for transmission of optical signals, a transparent element adapted to be aligned with the aperture for transmission of optical signals, at least one side of the transparent element facing the external environment; and a transparent conductive layer covering at least a portion of the transparent element, wherein responsive to the application of electrical power to the transparent conductive layer, the transparent conductive layer generates heat that is thermally communicated to the least one side of the transparent element facing the external environment.

Referring now to FIG. 3B, the primary housing 250 of the optical device is shown. It is appreciated that the primary housing 250 supports and surrounds the optical components 220, such as a prism and other components necessary to support the functionality of the optical device. The primary housing 250 includes an aperture 352 in the primary housing. Optical signals may be transmitted and received between the aperture 352 of the primary housing 250 and the patient's body cavity.

Referring now to FIG. 3C shows coupling of the secondary housing 310 with the primary housing 250 in accordance with one embodiment. In the embodiment shown in FIG. 3C, the primary housing 250 is positioned inside of the secondary housing 310 so that the secondary housing acts as a protective sleeve to protect the primary housing 250. The aperture of the primary housing 352 is positioned to align with the aperture 340 of the secondary housing. The transparent defogging element is also aligned with the aperture 340 of the secondary housing, thus enabling optical signals to be communicated from the optical instrument to the external environment. The defogging element 100 is held in place by the supports 320 of the secondary housing. The internal surface of defogging element 232 faces the aperture of the primary housing 352. The external surface of defogging element 234 faces and contacts the external environment 295.

In the embodiment shown in FIGS. 3A-3C, when the primary housing is coupled to the secondary housing as shown in FIG. 3C, the electrical connectors 260 shown on the bottom of the primary housing in FIG. 3B make electrical connection to the defogging element 100. In one example, the transparent conductive layer is applied to the internal surface 232 of the transparent element. In one embodiment, no dielectric layer covers the transparent conductive layer on the internal surface 232 and electrical contact is made directly from the electrical connectors 360 to the surface of the transparent conductive layer 120. In one example, the defogging element is similar to the defogging element in FIG. 1C and electrical connection is made from the electrical connectors 360 to the bus bars on the side of the defogging element. In another example, a dielectric layer (not shown) covers the transparent conductive layer and electrical contact is made from the connectors 360 to electrical bars which are connected to the transparent conductive layer.

In an alternative embodiment, instead of the transparent conductive layer being applied to the internal surface 232 of the transparent element—it can be applied to the external surface 234 of the transparent element. In this case, an electrical connection from the electrical connectors 360 on the base of the primary housing to the electrically conductive layer on the external surface of the transparent element would need to be made in order to provide power to the electrically conductive layer. It is appreciated that instead of having electrical connectors 360, other types of connectors may be used, such as the spring connectors described in FIG. 1B. Furthermore, power may be supplied to the defogging element 100 through other means, e.g., magnetic field, optically, etc., as discussed above, thereby eliminating the need to have electrical connectors.

The thermal defogging element may include a transparent element coated with a transparent conductive layer configured to generate heat in response to the application of power. For example, supplying power to the defogging element 100 via the electrical connectors 260 generates a heat flux due to the transparent conductive layer 120 (FIG. 1A) and its associated resistance. In one embodiment, the generated heat flux dissipates uniformly through the transparent substrate 110 (FIG. 1A) of the defogging element 100. In one embodiment, the transparent conductive layer is configured to reach a predetermined temperature in response to receiving power. The predetermined temperature of the transparent conductive layer is operable to prevent condensation from forming on the external surface of the thermal defogging element. As such, condensation formed on the external surface of the defogging element 234 due to a difference in temperature of the ambient air and the body cavity is substantially reduced and/or eliminated. In applications to patient's mouth, oral cavity is approximately 36.5° C. Thus, heating the defogging element 100 to 38° C. eliminates condensation and fog formed on the external surface of the defogging element 234.

It is appreciated that the temperature of the defogging element 100 in the device may be controlled using a controller, discussed below. Moreover, the thermal defogging element of the device may be programmed to reach and maintain a predetermined temperature depending on its application and the surrounding temperature. Furthermore in various embodiments, the temperature may be controlled manually, thereby allowing an operator to adjust defogging performance according to, for example, individual preference. Temperature control of the thermal defogging element is described in more detail with respect to FIGS. 6 and 7 below.

In one embodiment, the defogging system can be described by the implementation shown in FIG. 3A. For this case, the defogging system is the secondary housing that acts as an external sleeve that fits over the primary housing of the optical instrument. In the implementation shown in FIG. 3A, the defogging element is supported by the secondary housing. Referring to the defogging system shown in FIG. 3A is comprised of: a secondary housing, the secondary housing defining an aperture for transmission of optical signals, a defogging element comprised of a transparent element and a transparent conductive layer, wherein the defogging element is adapted to be aligned with the aperture of the secondary housing and an aperture of a primary housing, wherein the transparent conductive layer of the defogging element covers an area at least as large as the optical footprint of the transmitted optical signal through the transparent element, wherein at least one side of the defogging element faces the external environment, wherein responsive to the application of electrical power to the transparent conductive layer, the transparent conductive layer generates heat that is thermally communicated to the least one side of the defogging element facing the external environment.

Figure 4A:
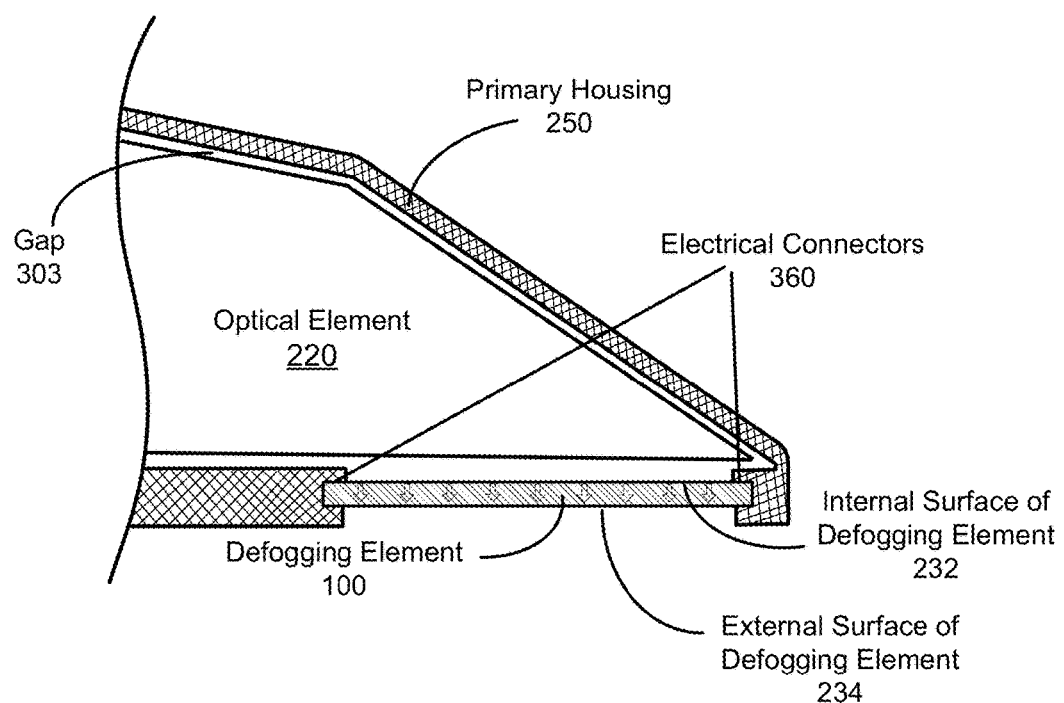
FIGS. 4A-4D show a device with a thermal defogging system according to an alternative embodiment.
Figure 4B:
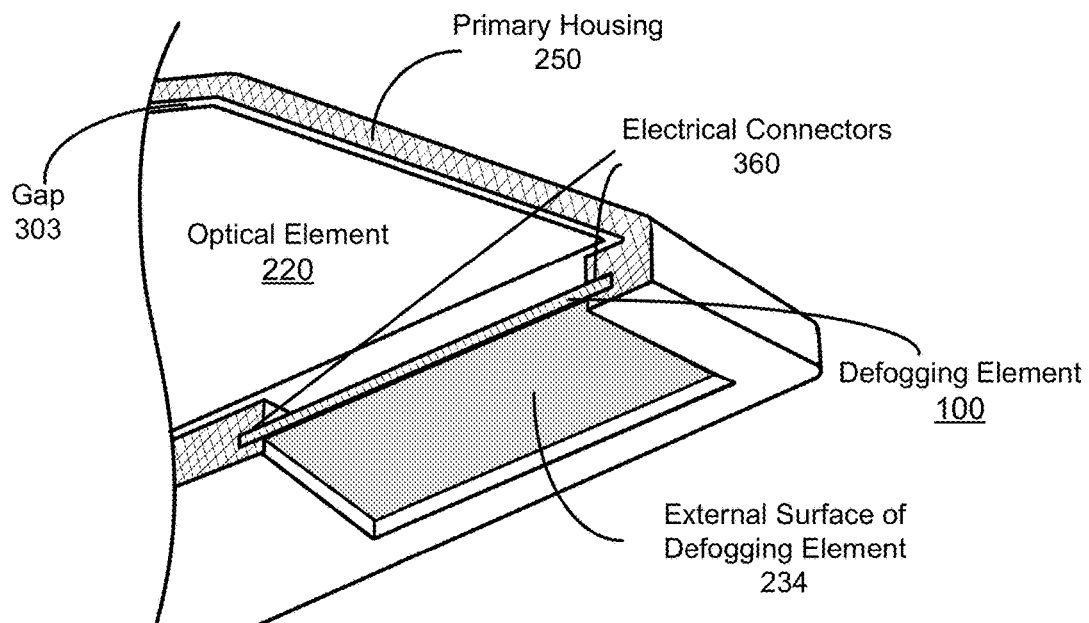
Figure 4C:
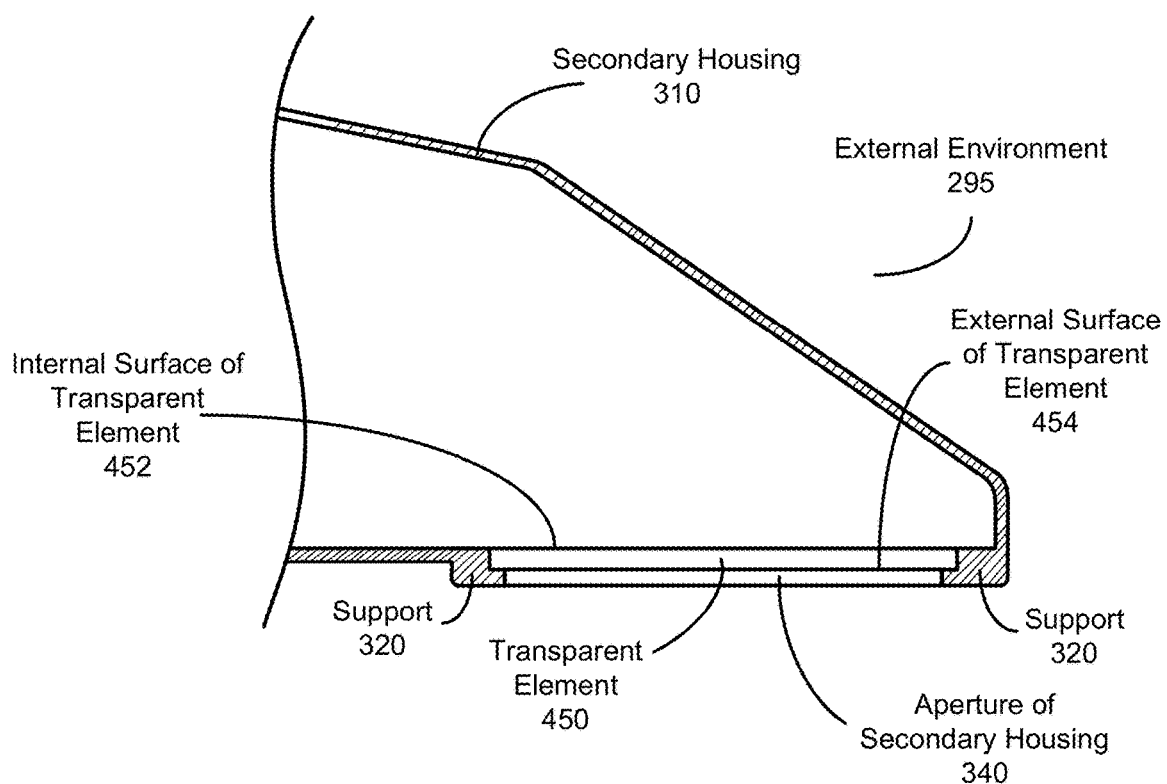
Figure 4D:
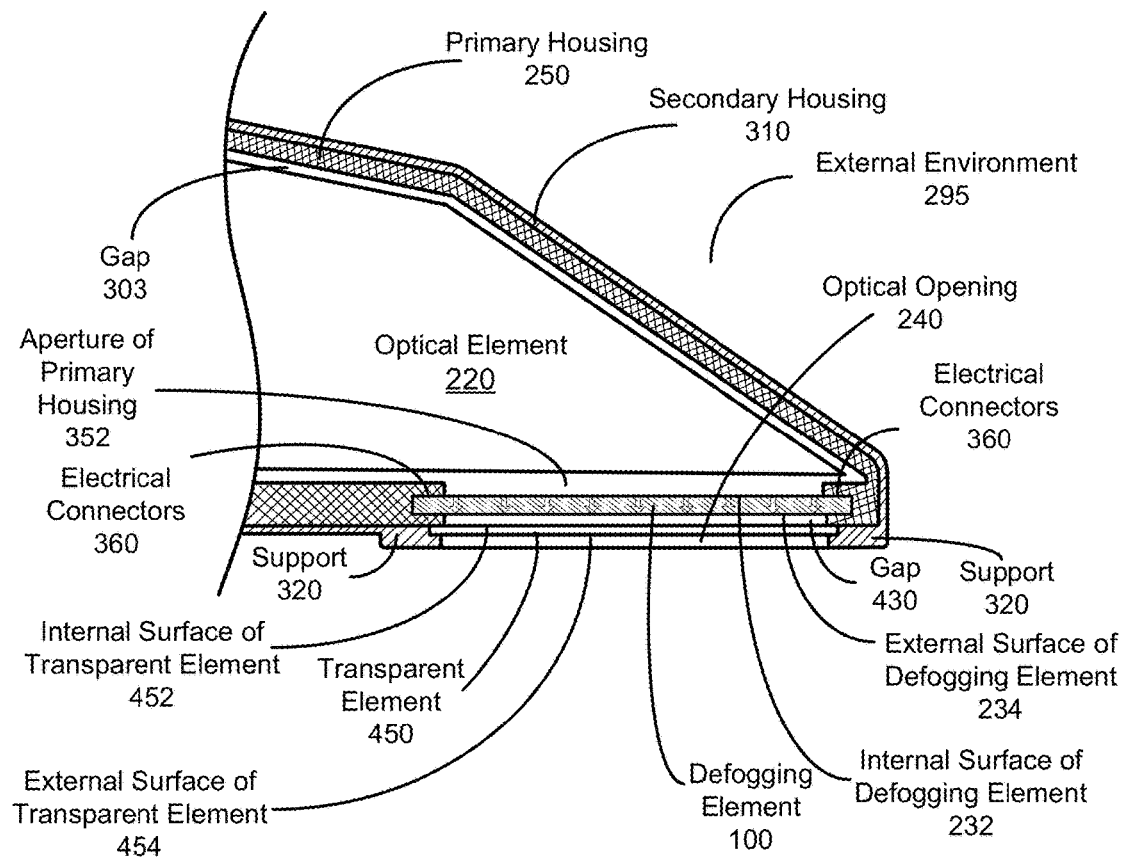

In an alternative embodiment, the defogging system can be described by the implementation shown in FIGS. 2C and 2D in that it is comprised of: at least a primary housing, the primary housing defining an aperture for transmission of optical signals, a transparent element adapted to be aligned with the window aperture for transmission of optical signals, at least one side of the transparent element facing the external environment; and a transparent conductive layer covering an area at least as large as the optical footprint of the transmitted optical signal through the transparent element, wherein responsive to the application of electrical power to the transparent conductive layer, the transparent conductive layer generates heat that is thermally communicated to the least one side of the transparent element facing the external environment. Referring now to FIGS. 4A-4D, shows parts of a thermal defogging system according to an alternative embodiment. FIGS. 4A and 4B illustrate different exemplary perspectives of the primary housing 4. FIG. 4C shows the secondary housing of a device, and FIG. 4D shows coupling of the primary housing and the secondary housing.

Referring now to FIGS. 4A-4D shows parts of a thermal defogging system according to one embodiment. The embodiment shown in FIGS. 4A-4D is similar to the embodiment shown in FIGS. 3A-3C, except that in the embodiment shown in FIGS. 4A-4D, the secondary housing does not include a defogging element. Instead the defogging element is integrated into the primary housing of the optical instrument—similar to as shown in FIGS. 2C-2D. In the embodiment shown in FIGS. 4A-4D, instead of having a defogging element—the secondary housing has a transparent element or window that is aligned with the aperture in the primary housing so that optical signals can be transmitted from the optical device to the external environment. The secondary housing forms a protective sleeve similar to that of the secondary housing described with respect to the FIGS. 3A-3C. In the embodiment shown in FIG. 4D, where the primary housing is coupled to the secondary housing, heat is thermally communicated from the defogging element that is supported by the primary housing, to the external surface of the transparent element or window in the secondary housing.

Referring to FIGS. 4A and 4B show different views of the primary housing of the optical instrument. The optical instrument includes a primary housing 250, a defogging element 100, and electrical connectors 360. In one example, the defogging element 100 is substantially similar to previously described thermal defogging elements. The primary housing 250 may house optical elements 220 (i.e. prism, power source, actuator, etc.), which make up the components of an optical instrument such as a scanning device, scope, etc.

In the example shown in FIGS. 4A-4B, electrical connection is made via electrical connectors 360. The electrical connectors 360 shown in FIGS. 4A-4B provide electrical connection to the defogging element 100. It is appreciated that instead of having electrical connectors 360 other types of connectors may be used such as the ones described in FIGS. 1C and 1E-H. Furthermore, it is appreciated that power may be supplied through other means, e.g., magnetic field, optically, etc., as discussed above, thereby eliminating the need to have electrical connectors. Power supplied to the defogging element 100 causes the conductive coating of the defogging element 100 to heat up.

Referring to FIGS. 4A and 4B, shows a defogging element 100 that is aligned with an aperture formed by the primary housing. In the embodiment shown in FIGS. 4A and 4B, the defogging element is transparent and is positioned within the aperture of the primary housing 250 of the optical instrument. The transparency of the defogging element 100 allows optical signals to travel between an optical element 220 of the optical device to the external environment without significant optical signal degradation. The internal surface 232 of defogging element faces the optical element 220 within the optical device. The external surface 234 of defogging element faces the external environment 295. Furthermore, the defogging element 100 is not limited to the illustrated horizontal configuration. For example, the defogging element 100 may be positioned such that it is angled to have particular properties, e.g., refracting properties, reflecting properties, light index matching properties, etc.

Referring now to FIG. 4C shows a secondary housing 310 of an optical device according to one embodiment is shown. The implementation shown in FIG. 4C is similar to the implementation shown in FIG. 3A, except that in FIG. 4C instead of a defogging element—a transparent element 450 is aligned with and is positioned to cover the aperture 340 of the secondary housing. The defogging system shown in FIG. 4C includes a secondary housing 310, supports 320, and a transparent element 450. The supports 320 are attached to or extend from the secondary housing 310 and hold the transparent element 450 in place. In one embodiment, the transparent element 450 is a substrate similar to that described in FIG. 1A comprised of a material having high optical transmission properties such as glass, plastic, polycarbonate, etc. Referring now to FIG. 4D shows coupling of the secondary housing to the primary housing so that the primary housing fits inside and is physically located inside of the secondary housing according to one embodiment. In this embodiment, at least a portion of the primary housing 250, the defogging element 100, and its electrical connectors 360 are all surrounded by the secondary housing 210 with its supports 220 holding the transparent element 450 in place. According to one embodiment, a gap 430 is formed between the transparent element 450 and the defogging element 100. For example, the gap may be 0.3 mm.

In one embodiment, the gap 430 contains air. However, it is appreciated that the gap may be filled with other gases or liquids as long as it does not substantially interfere with optical signal transmissions. Furthermore, the gap may be filled with other gases or liquids as long as it maintains proper heat transfer from the thermal defogging element 100 to the transparent element 450. It is appreciated that a different thickness of the gap 430 may be used based on the heat power generated by the defogging element 100. For example, the thickness of the gap 430 may be increased if the heat power generated is increased. It is appreciated that the thickness of the defogging element 100 and the thickness of the transparent element 450 may also be changed depending on the heat power generated by the defogging element 100. For example, a thickness of the thermal defogging element 100 is selected to ensure that heat is sufficiently transferred from one end to the other end of the thermal defogging element 100. It is noteworthy, that the thickness of the transparent element 450 may also depend on its application and its mechanical load. For example, the transparent element 450 must be thick enough to prevent it from breaking when in use.

Referring to FIG. 4D for example, the defogging element 100 is held in place and is in contact with the electrical connectors 360. As such, when power is supplied, the electrical connectors 360 provide the power to the conductive layer 120 (FIG. 1A) of the defogging element 100. The resistance of the transparent conductive layer 120 (FIG. 1A) of the defogging element 100 generates a heat flux that dissipates uniformly through the transparent substrate 110 (FIG. 1A) of the defogging element 100. In the embodiment shown in FIG. 4D, the defogging element 100 is separated from the transparent element 450 associated with the secondary housing 310 via a gap 303. The generated heat from the conductive layer 120 is transferred from the defogging element to the transparent element of the secondary housing via a gap 303.

For the case where the conductive layer 120 is formed on the internal surface of the defogging element, the generated heat flux is thermally communicated from the internal surface 232 of the defogging element to the external surface of defogging element 234 through the gap 430 to the internal surface of transparent element 452. Heat is then thermally communicated through the transparent element 450 and flows to the external surface 454 of the transparent element. As such, condensation formed on the external surface of transparent element 454 due to a difference in temperature of the ambient air and the body cavity is reduced. In one example, the oral cavity is approximately 36.5° C. and heating the defogging element 100 to 38° C. eliminates condensation and fog formed on the external surface 454 of transparent element 450.

The secondary housing 310 prevents fluids and other contaminants from reaching the primary housing 250 of the optical instrument. The secondary housing 310 and the transparent element 450 of the secondary housing may be removable. For example, the secondary housing 310 may be removed, disinfected, and reused for different patients. In an alternative embodiment, the secondary housing may be disposable and replaced with a new one for each patient. Further, it is appreciated that transparent element 450 may also be removed to be disinfected and/or disposed and replaced. Referring to the implementation shown in FIG. 4C, the defogging system shown can be described as a secondary housing, the secondary housing defining a window for transmission of optical signals; and a transparent element 450 housed within the secondary housing 310, the transparent element 450 adapted to be aligned with the aperture of the secondary housing and with a defogging element that is aligned with the aperture of a primary housing of an optical device for generating optical signals, wherein responsive to the application of power to a transparent conductive layer of the defogging element, the transparent conductive layer generates heat that is thermally communicated to the external surface of the transparent element housed within the secondary housing.

It is appreciated that the temperature of the defogging element 100 may be controlled using a controller, discussed below. Moreover, it is appreciated that the medical device may be programmed to reach and maintain a desired temperature depending on its application and the surrounding temperature. Temperature control of the defogging element is described in more detail with respect to FIGS. 5 and 6 below.

Figure 5A:
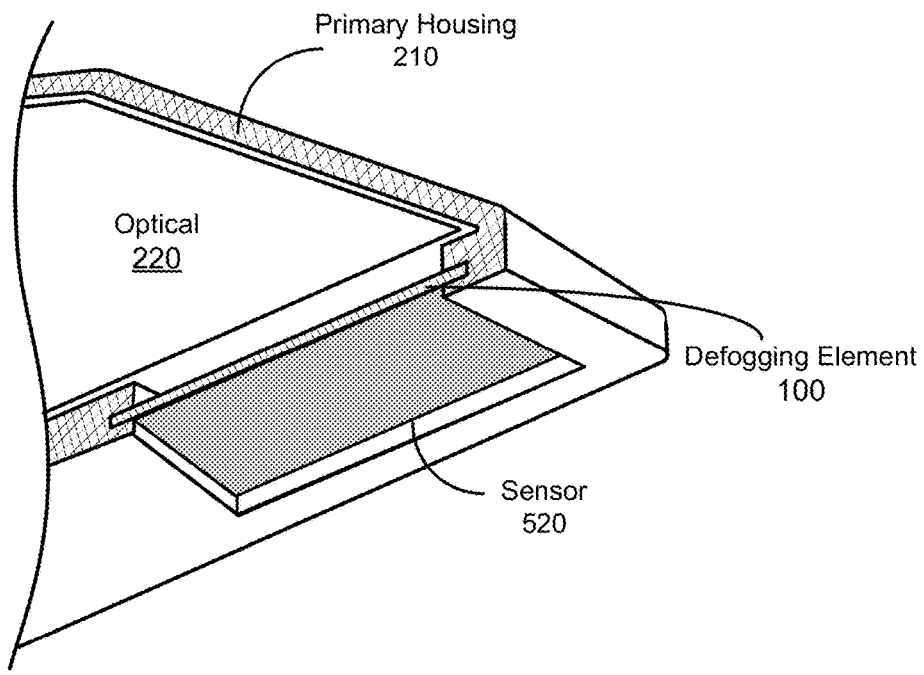
FIGS. 5A-5C show positioning of temperature sensors associated with the thermal defogging element according to various embodiments.
Figure 5B:
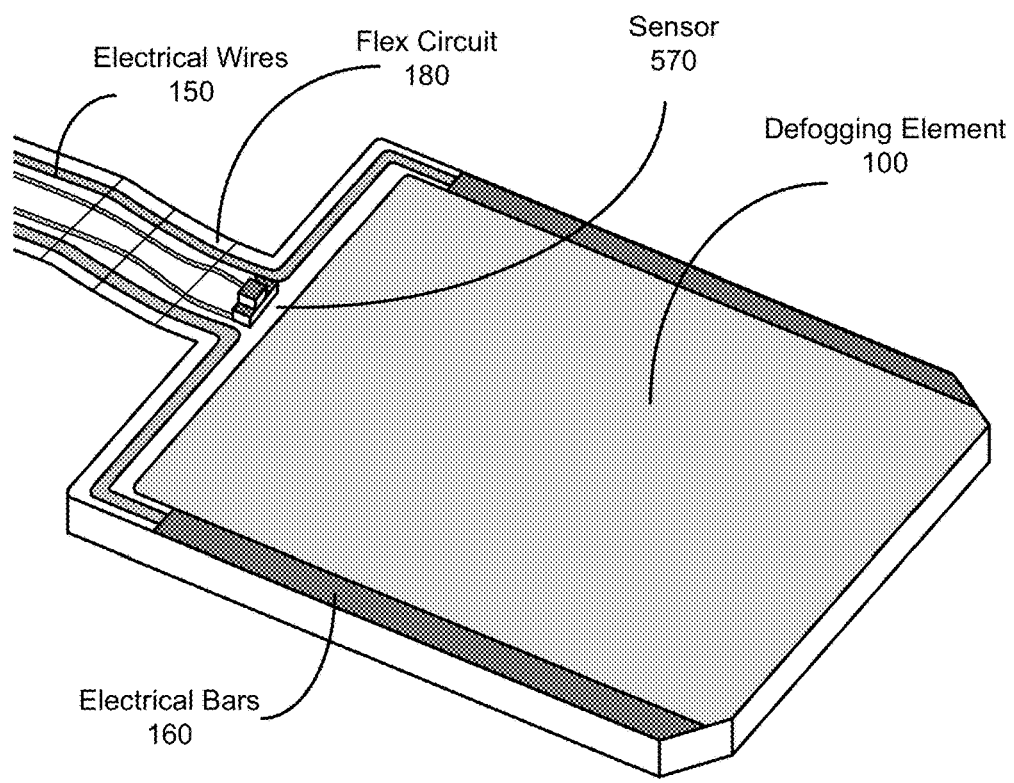
Figure 5C:
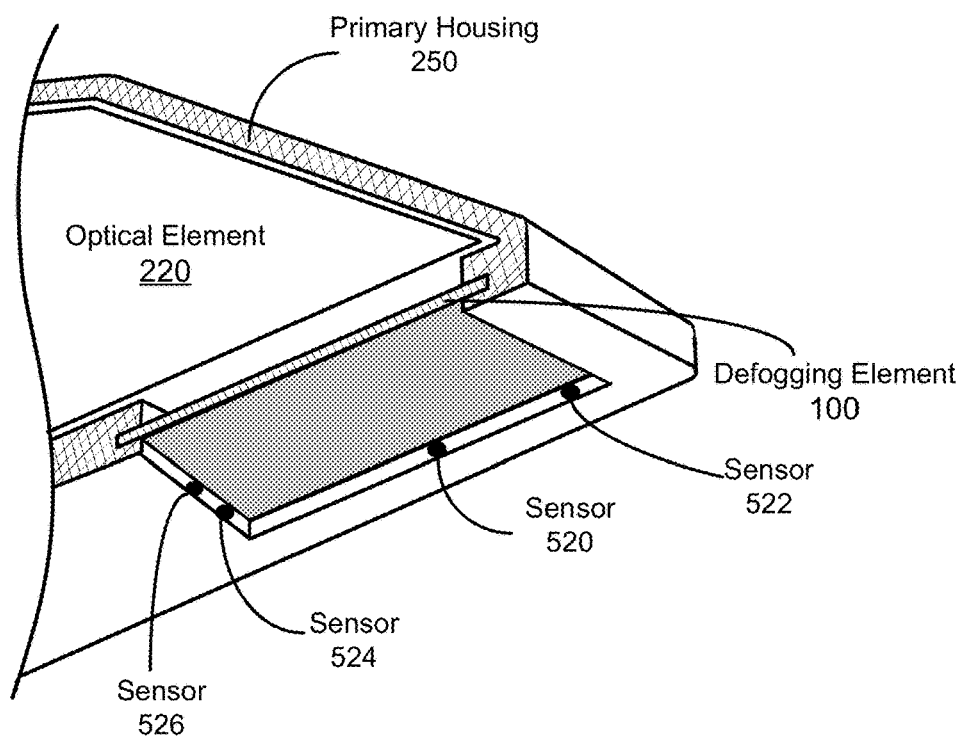

Referring now to FIGS. 5A-5C, positioning of temperature sensors associated with the thermal defogging element according to various embodiments is shown. In FIG. 5A, a primary housing 210, a defogging element 100, and a sensor 520 are shown. The primary housing 210 may be similar to that of FIGS. 2A-2D, 3A-3C, 4A-4D. The defogging element 100 is similar to the thermal defogging element, as described above. In one embodiment, the sensor measures the temperature associated with transparent element 110. In an alternative embodiment, the sensor 520 measures the temperature associated with the conductive coating layer 120 (FIG. 1A) of the thermal defogging element 100. The sensor 520 may be positioned in close proximity to a side facet of the defogging element and away from electrical bars. The sensor 520 may be a thermo resistor that changes its resistance in different temperatures, thereby measuring the temperature. In another embodiment, the sensor 520 may be thermocouple sensor with two dissimilar conductors in contact to generate a voltage when heated. It is appreciated that in one embodiment, the sensor 520 may be touching the side of the thermal defogging element 100 facing the optical element 220. In an alternative embodiment, the sensor may be touching the side of the thermal defogging element facing the external environment. In one embodiment, the sensor 520 may be an optical sensor configured to sense infrared radiation from a heated object, thereby measuring the temperature. The sensor 520 may or may not touch the upper layer of the thermal defogging element 100 if an optical sensor is used. It is appreciated that use of one sensor is exemplary and not intended to limit the scope of the embodiments. For example, two or more sensors may be used positioned in different locations to obtain a better average measurement of the temperature.

Referring now to FIG. 5B, a thermal defogging element 100 similar to that of FIG. 1C is shown. In this embodiment, a sensor 570 is positioned on a side facet of the thermal defogging element away from the electrical bars 160. It is appreciated that the sensor may be a thermo resistor, a thermocouple sensor, or an optical sensor, to name a few.

Referring now to FIG. 5C, a thermal defogging element according to one embodiment is shown having more than one temperature sensor. For example, the thermal defogging element 500C may include sensors 520, 522, 524, and 526. As discussed above, a number of different sensors may be used. For example, the sensors 520, 522, 524, and 526 may be a combination of a thermo resistor, a thermocouple sensor, or an optical sensor, to name a few. It is appreciated that particular sensors mentioned above are merely exemplary and not intended to limit the scope of the embodiments. The temperature measured by the sensors in this embodiment may be averaged to obtain a more accurate measurement. In a different embodiment, the highest and the lowest measure temperature may be discarded and the remaining measured temperatures may be averaged.

It is appreciated that in one embodiment, the sensor is configured to detect temperature associated with the generated heat. In one embodiment, the sensor is selected from a group consisting of thermal resistor sensor, a thermocouple sensor, and an optical sensor. The controller is configured to adjust the power provided to the thermal defogging element based on the detected temperature.

Referring now to FIG. 6 shows a thermal defogging system 600 according to one embodiment. The system 600 may include a controller 610, one or more sensors 620, a defogging element 630, and a power supply 640. The defogging element 630 and the one or more sensors 620 operate substantially similar to those discussed above. In this embodiment, one or more sensors 620 measure the temperature of the defogging element 630 of the thermal defogging element. It is appreciated that in an alternative embodiment, the temperature of the conductive coating layer of the defogging element may be measured. In one embodiment, the temperature of the transparent substrate of the thermal defogging element may be measured.

In one embodiment, the measured temperature is communicated to the controller 610. The controller 610 may include a computer readable medium to execute instructions based on the measured temperature. In one embodiment, the desired temperature for removing condensation may be either hardcoded into the controller 610 or it may be entered by the user. For example, a desired temperature for removing condensation from oral cavity may be 38° C. The controller 610 may fetch the desired temperature from a memory component and compare the measured temperature to that of the desired temperature. In response to a difference in temperature the controller 610 may adjust the amount power supplied to the thermal defogging element 630. For example, if the measured temperature is below 38° C., the controller 610 may cause the power supply 640 to provide more power to the defogging element 630. On the other hand, if the measured temperature is above 38° C., the controller 610 may cause the power supply 640 to stop providing power to the defogging element 630.

It is appreciated that according to one embodiment, the activation voltage of the thermal defogging element may be between 4-6 Volts. The resistance of the conductive coating layer 120 may be between 40 to 60 ohms. As such, between 0.4 W to 0.6 W power may be provided to the thermal defogging element. According to one embodiment, it may take 20-40 seconds to heat the thermal defogging element 630 to 38° C. when the temperature of the body cavity, e.g., oral cavity, is 36.5° C. It is appreciated in different applications the heating of the thermal defogging element may take more or less time depending on the temperatures (desired temperature and measured temperature), resistance of the defogging element 630, and the amount of power supplied.

It is appreciated that initiation of temperature measurement may be automatic or manual. For example, the sensors and adjustment of power to the thermal defogging element may occur automatically in response to the device being turned on. On the other hand, the sensors and adjustment of power to the thermal defogging element may occur in response to a user selection. For example, the user may initiate the defogging function by pressing a button. It is also appreciated that initiation of thermal defogging functionality may automatically occur in response to detecting that the housing containing the optical instrument has moved. For example, a gyroscope or an accelerometer may be used to detect movement.

Embodiments described herein with respect to FIGS. 6 and 7 may be discussed in the general context of computer-executable instructions residing on some form of computer-readable storage medium, such as program modules, executed by one or more computers, computing devices, or other devices. By way of example, and not limitation, computer-readable storage media may include computer storage media and communication media. Generally, program modules include routines, programs, objects, components, data structures, etc., that perform particular tasks or implement particular abstract data types. The functionality of the program modules may be combined or distributed as desired in various embodiments.

Computer storage media can include volatile and non-volatile, removable and non-removable media implemented in any method or technology for storage of information such as computer-readable instructions, data structures, program modules, or other data. Computer storage media can include, but is not limited to, random access memory (RAM), read only memory (ROM), electrically erasable programmable ROM (EEPROM), flash memory, or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can be accessed to retrieve that information.

Communication media can embody computer-executable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media can include wired media such as a wired network or direct-wired connection, and wireless media such as acoustic, radio frequency (RF), infrared and other wireless media. Combinations of any of the above can also be included within the scope of computer-readable storage media.

Referring now to FIG. 7, an exemplary flow diagram 700 of operation of a thermal defogging element according to one embodiment is shown. At step 710, power is supplied to the defogging element in order to heat up the defogging element. At step 720, the temperature associated with the defogging element may be measured. At step 730, the measured temperature may be compared with the desired temperature (user entered or hardcoded). According to one embodiment, the desired temperature may be fetched from a memory component storing the value. The controller, at step 730, may adjust the amount of power supplied to the defogging element in order to adjust the temperature of the defogging element. For example, more power may be provided to the defogging element if the measured temperature is below the desired temperature.

Accordingly, condensation and fog formed on the exterior of a transparent substrate, e.g., the thermal defogging element, the transparent window, etc., that is in contact with patient's body cavity may be reduced by heating up the thermal defogging element. Moreover, using the thermal defogging element eliminates the need to use a heater within the medical device and using a fan to blow air, thereby reducing the size of the medical device while eliminating noise generation. Furthermore, using the thermal defogging element does not interfere with optical signals and it further reduces the amount of power being used by the device to remove the condensation.

The foregoing description, for purpose of explanation, has been described with reference to specific embodiments. However, the illustrative discussions above are not intended to be exhaustive or to limit the embodiments to the precise forms disclosed. Many modifications and variations are possible in view of the above teachings.

What is claimed is:

1. An optical scanning device comprising:
   an optical element for transmission of optical signals;
   a primary housing that houses the optical element, the primary housing comprising a head configured for insertion into a patient oral cavity, the head of the primary housing defining an aperture for transmission of the optical signals; and
   a defogging element coupled to the primary housing, the defogging element comprising:
      a transparent element positioned within the aperture, at least one side of the transparent element facing an external environment; and
      a transparent conductive layer covering an area on a surface of the transparent element, the area of the transparent conductive layer having a size that at least partially covers an optical footprint of the transparent element for the optical signals to be transmitted through the transparent element; and
   a disposable sleeve coupled to and covering the head of the primary housing, wherein the disposable sleeve protects the optical scanning device from contact with the patient oral cavity, the disposable sleeve comprising:
      an additional aperture that aligns with the aperture; and
      an additional transparent element in the additional aperture, the additional transparent element lacking a conductive layer;
      wherein an air gap separates the additional transparent element from the transparent element, and wherein responsive to application of electrical power to the transparent conductive layer, the transparent conductive layer generates heat that is thermally communicated across the air gap to the additional transparent element to defog the additional transparent element of the disposable sleeve.

2. The optical scanning device recited in claim 1, wherein the defogging element is removably coupled to the primary housing.

3. The optical scanning device recited in claim 1, wherein the defogging element is a component of the primary housing.

4. The optical scanning device recited in claim 1, wherein the transparent conductive layer is applied to an internal surface of the transparent element.

5. The optical scanning device recited in claim 1, wherein the transparent conductive layer is applied to an external surface of the transparent element.

6. An optical instrument comprising:
an optical element for transmission of optical signals;
a primary housing that houses the optical element, the primary housing comprising a head configured for insertion into a patient oral cavity, the head of the primary housing defining an aperture for transmission of the optical signals;
a defogging element coupled to the head of the primary housing, the defogging element comprising:
    a transparent element positioned within the aperture, at least one side of the transparent element facing an external environment; and
    a transparent conductive layer covering an area on a surface of the transparent element; and
a removable secondary housing coupled to and covering the head of the primary housing, the removable secondary housing defining a second aperture for transmission of the optical signals, wherein the removable secondary housing comprises an additional transparent element in the second aperture, the additional transparent element lacking a conductive layer, wherein an air gap separates the additional transparent element from the transparent element, and wherein responsive to application of electrical power to the transparent conductive layer, the transparent conductive layer generates heat that is thermally communicated across the air gap to a side of the additional transparent element facing the external environment.

7. The optical instrument recited in claim 6, wherein a portion of the primary housing fits within the secondary housing.

8. The optical instrument recited in claim 6, wherein the optical instrument is a medical device and the removable secondary housing is disposable after each use.

9. An optical scanning device comprising:
an optical element for transmission of optical signals;
a primary housing that houses the optical element, the primary housing comprising a head that is to be inserted into a patient cavity, the head of the primary housing defining an aperture for transmission of the optical signals; and
a defogging element mounted to the primary housing, the defogging element comprising:
    a transparent element positioned within the aperture, at least one side of the transparent element facing an external environment; and
    a transparent conductive layer covering at least a portion of the transparent element; and
a secondary housing coupled to and covering the head of the primary housing, wherein the secondary housing protects the optical scanning device from contact with the patient cavity, the secondary housing comprising:
    an additional aperture that aligns with the aperture; and
    an additional transparent element in the additional aperture;
    wherein an air gap separates the additional transparent element from the transparent element, and wherein responsive to application of electrical power to the transparent conductive layer, the transparent conductive layer generates heat that is thermally communicated across the air gap to the additional transparent element to defog the additional transparent element of the secondary housing.

10. The optical scanning device recited in claim 9, wherein an area of the transparent conductive layer has a size that at least partially covers an optical footprint of the transparent element for the optical signals to be transmitted through the transparent element.

11. The optical scanning device recited in claim 9, wherein the transparent conductive layer covers an area at least as large as the aperture of the primary housing.

12. The optical scanning device of claim 1, wherein the defogging element has a substantially rectangular shape, the optical scanning device further comprising:
a flex circuit that connects to electrical bars on a surface of the defogging element.

13. The optical scanning device of claim 12, further comprising:
a temperature sensor attached to the defogging element.

* * * * *